US008299072B2

(12) United States Patent
Nam et al.

(10) Patent No.: US 8,299,072 B2
(45) Date of Patent: Oct. 30, 2012

(54) PYRAZOLYLMETHYLAMINE COMPOUNDS AS CALCIUM CHANNEL MODULATORS AND PREPARATION METHOD THEREOF

(75) Inventors: Ghilsoo Nam, Nowon-gu (KR); Kyung Il Choi, Seoul (KR); Hye Ran Kim, Seoul (KR); Seon Hee Seo, Seoul (KR); Yoon Jee Kim, Seoul (KR); Hee Sup Shin, Seoul (KR); Dong Jin Kim, Seoul (KR); Ae Nim Pae, Seoul (KR); Hye Jin Chung, Seoul (KR); Hyunah Choo, Seoul (KR); Hyewhon Rhim, Seoul (KR); Yong Seo Cho, Seoul (KR); Eun Joo Roh, Seoul (KR); Gyo Chang Keum, Seoul (KR); Kee Hyun Choi, Guri-si (KR); Kye Jung Shin, Seoul (KR); Hoh Gyu Hahn, Seoul (KR); Chan Seong Cheong, Seoul (KR); Jae Kyun Lee, Seoul (KR); Kee Dal Nam, Seoul (KR); Yong Koo Kang, Seoul (KR); Youngsoo Kim, Yongin-si (KR); Woong Seo Park, Seoul (KR); Eunice Eun-Kyeong Kim, Seoul (KR); Key-Sun Kim, Seoul (KR); Hesson Chung, Incheon (KR); Dong Yun Shin, Seoul (KR); Chi man Song, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 292 days.

(21) Appl. No.: 12/568,243

(22) Filed: Sep. 28, 2009

(65) Prior Publication Data

US 2010/0094006 A1 Apr. 15, 2010

(30) Foreign Application Priority Data

Oct. 15, 2008 (KR) .................. 10-2008-0101249

(51) Int. Cl.
*A61K 31/496* (2006.01)
*A61K 31/506* (2006.01)
*A61K 31/5377* (2006.01)
*C07D 231/12* (2006.01)
*C07D 401/04* (2006.01)
*C07D 403/12* (2006.01)
*C07D 405/12* (2006.01)
*C07D 405/14* (2006.01)
*C07D 413/10* (2006.01)

(52) U.S. Cl. ........... 514/235.8; 514/252.19; 514/253.09; 514/254.05; 514/254.07; 544/121; 544/295; 544/364; 544/371

(58) Field of Classification Search .................. None
See application file for complete search history.

(56) References Cited

U.S. PATENT DOCUMENTS 7,544,686 B2 * 6/2009 Nam et al. ............... 514/253.09

FOREIGN PATENT DOCUMENTS

| KR | 10-2005-0084739 A | 8/2005 |
|---|---|---|
| KR | 10-2006-0026315 | 3/2006 |
| KR | 100654328 B | 11/2006 |
| WO | WO 2006/024160 A | 3/2006 |
| WO | WO 2007/137417 A | 12/2007 |

OTHER PUBLICATIONS

Dogrul, Ahmet et al.: "Reversal of experimental neuropathic pain by T-type calcium channel blockers", *Pain*, 105 (2003) pp. 159-168.
Daesoo Kim et al.: "Thalamic Control of Visceral Nociception Mediated by T-Type Ca 2+Channels", *Science*, 302, (2003), pp. 117-119.
Flatters, Sarah J.L. et al.: "Ethosuximide reverses paclitaxel- and vincristine-induced painful peripheral neuropathy", *Pain*, 109 (2004) pp. 150-161.
Flatters, Sarah J.L.: "T-type calcium channels: a potential target for the treatment of chronic pain", *Drugs of the Future*, 2005, 30(6), pp. 573-580.
Barton, Matthew E. et al.: "The antihyperalgesic effects of the T-type calcium channel blockers ethosuximide, trimethadione, and mibefradil", *European Journal of Pharmacology*, 521 (2005), pp. 79-85.
Viskoper, Rj et al.: "A randomized, double-blind trial comparing mibefradil and amlodipine: two long-acting calcium antagonists with similar efficacy but different tolerability profiles", *Journal of Human Hypertension*, 1997, 11, pp. 387-393.
Mishra, Santosh K. et al.: "Selective Inhibition of T-type $Ca^{2+}$Channels by Ro 40-5967", *Circulation Research*, vol. 75, No. 1, Jul. 1994, pp. 144-148.
Gray, Gillian A. et al.: "Effects of Calcium Channel Blockade on the Aortic Intima in Spontaneously Hypertensive Rats", *Hypertension*, vol. 22, No. 4, Oct. 1993, pp. 569-576.
Veniant, Murielle et al.: "Calcium blockade versus ACE inhibition in clipped and unclipped kidneys of 2K-1C rats", *Kidney International*, vol. 46 (1994), pp. 421-429.
Moosmang, Sven et al.: "Antihypertensive Effects of the Putative T-Type Calcium Channel Antagonist Mibefradil Are Mediated by the L-Type Calcium Channel $Ca_v1.2$", *Circulation Research*, Jan. 6/20, 2006, pp. 105-110.
Vitko, Iuliia et al.: "Functional Characterization and Neuronal Modeling of the Effects of Childhood Absence Epilepsy Variants of CACNA1H, a T-Type Calcium Channel", *The Journal of Neuroscience*, May 11, 2005, 25 (19), pp. 4844-4855.
Khosravani, Houman et al.: "Effects of $Ca_v3.2$ Channel Mutations Linked to Idiopathic Generalized Epilepsy", *Ann Neurol*, 2005, 57, pp. 745-749.
McGivern, Joseph G.: "Targeting N-type and T-type calcium channels for the treatment of pain", *DDT*, vol. 11, No. 5/6, Mar. 2006, pp. 245-253.
Yunker, Anne Marie R. et al.: "Low-Voltage-Activated ("T-Type") Calcium Channels in Review", *Journal of Bioenergetics and Biomembranes*, vol. 35, No. 6, Dec. 2003, pp. 533-575.
Carbone, E. et al.: "A low voltage-activated, fully inactivating Ca channel in vertebrate sensory neurons", *Nature*, vol. 310, Aug. 9, 1984, pp. 501-502.
Geduldig, D. et al.: "Voltage Clamp of the Aplysia Giant Neurone: Early Sodium and Calcium Currents", *J. Physiol.*, 1970, 211, pp. 217-244.

* cited by examiner

*Primary Examiner* — Emily Bernhardt

(74) *Attorney, Agent, or Firm* — Frommer Lawrence & Haug LLP; Ronald R. Santucci

(57) ABSTRACT

The present invention relates to pyrazolylmethylamine-piperazine derivatives and their pharmaceutically acceptable salts effective as calcium channel modulators and a method of manufacturing the same. The present invention also relates to the medicinal use of the above compounds as therapeutic treatment of diseases due to their effect as calcium channel modulators.

10 Claims, No Drawings

PYRAZOLYLMETHYLAMINE COMPOUNDS AS CALCIUM CHANNEL MODULATORS AND PREPARATION METHOD THEREOF

CROSS-REFERENCE TO RELATED APPLICATION

This application claims under 35 U.S.C. §119(a) the benefit of Korean Patent Application No. 10-2008-0101249 filed Oct. 15, 2008, the entire contents of which are incorporated herein by reference.

BACKGROUND

1. Technical Field

The present invention relates to pyrazolylmethylamine-piperazine derivatives and their pharmaceutically acceptable salts effective as calcium channel modulators and a method of manufacturing the same. The present invention also relates to the pharmaceutical use of the above compounds as therapeutic treatment of diseases due to their effect as calcium channel modulators.

2. Background Art

Introduction of calcium ions into cells through a voltage-gated calcium channel has been known to mediate a wide scope of cellular and physiological reactions including secretion of hormones, and gene expression. Since 1950s, the flux of calcium ions, expression and physiological importance of transmembrane have been well perceived, and in 1970s, it was made possible to measure the calcium current under voltage-clamp condition (D. Gedualding, R. Gruener, *J. Physiolo.* 1970, 211, 217-244). In 1980s, neuronal calcium channel, depending on the voltage dependence, was divided into two subtypes of high voltage activity (HVA) $Ca^{2+}$ channel (L, N, P, Q and R type) and low voltage activity (LVA) (T-, L-type) (R, Llinas, Y. Yarom, *J. Physiolo.* 1981, 315, 549-567, E. Carbone, H. D. Lux, *Nature*, 1984, 310, 501-502).

Further, LVA-dependent channel, based on its transient signal, was named as 'T-type calcium channel', while HVA-dependent channel, based on its long-lasting signal, was named as 'L-type calcium channel'.

The classification of these calcium channels and their systems thereof are as shown below in the Table 1.

TABLE 1

| Calcium channels | $Ca_v$ name | $\alpha_1$ subtype |
| --- | --- | --- |
| Type L | $Ca_v 1.1$ | $\alpha_{1S}$ |
|  | $Ca_v 1.2$ | $\alpha_{1C}$ |
|  | $Ca_v 1.3$ | $\alpha_{1D}$ |
|  | $Ca_v 1.4$ | $\alpha_{1F}$ |
| Type P or Q | $Ca_v 2.1$ | $\alpha_{1A}$ |
| Type N | $Ca_v 2.2$ | $\alpha_{1B}$ |
| Type R | $Ca_v 2.3$ | $\alpha_{1E}$ |
| Type T | $Ca_v 3.1$ | $\alpha_{1G}$ |
|  | $Ca_v 3.2$ | $\alpha_{1H}$ |
|  | $Ca_v 3.3$ | $\alpha_{1I}$ |

As shown in the above Table 1, HVA L-type calcium channel is indicated as $\alpha_{1S}$, $\alpha_{1C}$, $\alpha_{1D}$ and $\alpha_{1F}$ ($Ca_v 1.1$-$Ca_v 1.4$) subtypes.

As shown in the above Table 1, HVA L-type calcium channel is indicated as $\alpha_{1S}$, $\alpha_{1C}$, $\alpha_{1D}$ and $\alpha_{1F}$ ($Ca_v 1.1$-$Ca_v 1.4$) subtypes. HVA P-, Q-, N- and R-type calcium channels are indicated as subtypes of ($Ca_v 2.1$), $\alpha_{1B}$ ($Ca_v 2.2$), and $\alpha_{1E}$ ($Ca_v 2.3$), respectively.

LVA T-type calcium channels are indicated as subtypes of $\alpha_{1G}$, $\alpha_{1H}$ and $\alpha_{1I}$ ($Ca_v 3.1$-$Ca_v 3.3$). Further, these pore-forming a subtypes can bind to other auxiliary subtypes such as $\alpha_2 \delta$, $\beta$ or $\gamma$.

The above voltage-gated ion channels are very closely associated with secretion of neurotransmitters and are mainly discovered in central nervous system, peripheral nervous system and neuroendocrine cells.

All channels used and the neurotransmitters system are somehow involved in pain-signal transmission, and T- and N-type calcium channels are becoming a target for the development of a novel anesthesia.

Pains may be largely divided into acute, chronic and neuropathic pains. Of them, neuropathic pain is initiated or caused by nerve injury, and lesion or dysfunction in the nerves system can result from trauma, viral infection, drug-induced or cancer related condition. It is associated with abnormal sensory phenomena including allododynia and hyperalgesia. It cause sensitization of sensory fibers and awakening of silent nociceptor, and result in reorganization of spinal and cortical circuit which are associated with altered calcium channel expression. Because of the complexity and diversity of the pathophyological mechanisms in neuropathic pain, successful treatment remains difficult to predict and achieve.

Calcium channels are endogenous modulators and have been studied for their roles in relation to multiple neurotransmitter, hormone drugs, antihypertensive drugs, anesthetic drugs, antiarrhythmic drugs, antiepileptic drugs (A. M. Yunker, M. W. McEnery, *J. Bioeng. Biomembr.* 2003, 35, 533).

Recently, it was shown that N-type ($Ca_v 2.2$) and T-type calcium channels are valuable targets for pain treatment by the approval of Prialt® (Elan Pharmaceuticals), their selective blocker developed as a new synthetic drug (Drug Discovery Today, 2006, 11(5), 245-253).

In addition, $Ca_v 2.2$ also mediates the release of neurotransmitters from the neurons in the sympathetic nerve system, and antagonists can be used for the treatment of cardiovascular diseases such as hypertension, cardiac arrhythmia, angina pectoris, myocardial infarction and congestive heart failure.

Further, T-type calcium channel is involved in cell development, differentiation and proliferation, cancer growth, sleep, epilepsy, nociception, pain, neuropathic pain, etc., and thus control of the T-type calcium channel has become a target for the regulation of the above.

Further, T-type calcium channel is known to be present in CNS, cardiac and vascular smooth muscle, adrenal cortex, heart, etc., and the inhibitors of the T-type calcium channel is known effective in the treatment of cerebral diseases and cardiovascular diseases such as epilepsy, hypertension, angina pectoris, etc.; ① Hosravani, Houman et al., "Effects of Cav3.2 channel mutations linked to idiopathic generalized epilepsy", *Annals of Neurology* (2005), 57(5), 745-749; ② Vitko, Iuliia et al., "Functional characterization and neuronal modeling of the effects of childhood absence epilepsy variants of CACNA1H, a T-type calcium channel", *Journal of Neuroscience* (2005), 25(19), 4844-4855; ③ Moosmang, Sven et al., "Antihypertensive Effects of the Putative T-Type Calcium Channel Antagonist Mibefradil Are Mediated by the L-Type Calcium Channel Cav1.2", *Circulation Research* (2006), 98(1), 105-110; ④ Murielle Veniant et al., "Calcium blockade versus ACE inhibition in clipped and unclipped kidneys of 2K-1C rats", *Kidney International*, Vol 46, pp. 421-429; ⑤ Gillian A. Gray et al., "Effects of Calcium blockade on the Aortic Intima in Spontaneously Hypertensive Rats", *Hypertension*, Vol 22, No 4 October 1993; ⑥ Santosh K. Mishra et al., "Selective inhibition of T-Type $Ca^{2+}$ Channels by Ro 40-5967, *Circulation Reasearch*, Vol 75, No 1 Jul. 1994; ⑦ R J Viskoper et al., "Trial comparing mibefradil and amlodipine", *Journal of Human Hypertention* (1997) 11, 387-393.

Recently, the antagonists of T-type calcium channel were reported to be effective in pain treatment. For example, both mibefradil and ethosuximide have shown inhibition of mechanically and thermally evoked neuronal responses in spinal nerve ligation model of neuropathic in rats; ① Barton, Matthew E. et al. "The antihyperalgesic effects of the T-type calcium channel blockers ethosuximide, trimethadione, and mibefradil", *European Journal of Pharmacology* (2005), 521 (1-3), 79-85; ② Flatters, Sarah J. L., "T-type calcium channels: A potential target for the treatment of chronic pain", *Drugs of the Future* (2005), 30(6), 573-580; ③ Flatters, Sarah J. L. et al. "Ethosuximide reverses paclitaxel- and vincristine-induced painful peripheral neuropathy", *Pain* (2004), 109(1-2), 150-161; ④ Dogrul, Ahmet et al. "Reversal of experimental neuropathic pain by T-type calcium channel blockers", *Pain* (2003), 105(1-2), 159-168; Daesoo Kim et al. "Thalamic Control of Visceral Nociception Mediated by T-Type $Ca^{2+}$ Channels", *Science* Vol 302, 3 Oct. 2003.

USFDA approved or investigated drugs that act on the conventional inhibitors of N-type calcium channel are Gabapentin (Neurontin™) and Ziconotide (Prialt™) as antiepileptic and a neuropathic pain treatment. However, they have a rather low scope of therapeutic efficacies due to factors such as excess administration and patients' characteristics, and also there is a side effect of sedating activity in case of excess dosage.

Of the conventional T-type calcium channel inhibitors, Mibefradil (Ro 40-5967, WO 98/49149) had been used for the treatment of hypertension and angina pectoris. However, it is now withdrawn from market due to drug interactions leading to various adverse effects. It was shown that mibefradil inhibits cytochrome P-450 3A4 and 2D6, enzymes used to metabolize a number of therapeutic agents. Therefore, there is practically no selective T-type calcium channel inhibitor available at present, and thus it is imperative to develop an effective T-type calcium channel antagonist.

Calcium channel inhibitors, due to their close association with neuronal diseases, have been actively studied by large or mid-large sized pharmaceutical firms: e.g., urea derivatives (WO 2006/024260) and heterocyclic compounds (WO 2007/137417 A1) in Neuromed Technology, Inc.; 3,4-dihydroquinazoline derivatives (Korean Pat. No. 0610731), piperazinylalkylisoxazole derivatives (Korean Pat. No. 0616099), piperazinylalkylpyrazole derivatives (Korean Pat. No. 0654328).

Therefore, the inventors of the present invention have made various efforts to develop a novel compound to act in the calcium channel, and found that pyrazolylmethylamine-piperazine derivatives synthesized as a result thereof have excellent antagonistic effect against the T-type calcium channel thereby completing the present invention.

DISCLOSURE

Technical Problem

An objective of the present invention is to provide novel pyrazolylmethylamine-piperazine derivatives with various substitution groups and their pharmaceutically acceptable salts.

Another objective of the present invention is to provide a pharmaceutical composition for the treatment and prevention of cerebral diseases, cardiac diseases, or pain-related diseases comprising pyrazolylmethylamine-piperazine derivatives and their pharmaceutically acceptable salts as active ingredient capable of efficient blocking of T-type calcium channel.

Therefore, the novel compounds of the present invention are effective for the treatment of cerebral diseases such as epilepsy, depression, Parkinson's disease, dementia, and sleep disorder; cardiac diseases such as hypertension, cardiac arrhythmia, angina pectoris, myocardial infarction and congestive heart failure; and pain-related diseases such as chronic and acute pains, and neuropathic pains.

A further objective of the present invention is to provide a method for manufacturing the above-mentioned novel pyrazolylmethylamine-piperazine derivatives by reacting haloacetylpiperazine with pyrazolylmethylamine.

Another further objective of the present invention is to provide the above-mentioned novel pyrazolylmethylamine-piperazine derivatives by reacting piperazine with pyrazolylmethylcarbamoylmethyl halide.

A still another further objective of the present invention is to provide pyrazolylmethylcarboxamidomethyl halide as a novel intermediate.

Technical Solution

The present invention relates to pyrazolylmethylamine-piperazine derivatives represented by the formula 1 below and their pharmaceutically acceptable salts thereof effective for the treatment and prevention of cerebral diseases, cardiac diseases or pain-related diseases due to their selective antagonistic activity against T-type calcium channel.

[formula 1]

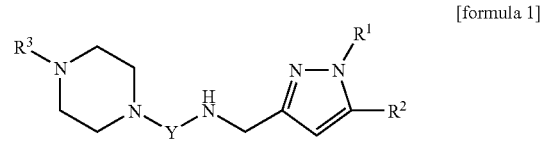

In the above formula 1,

Y represents —$(CH_2)_n$—C(O)—; or —C(O)—$(CH_2)_n$—, wherein n is an integer of 1-4;

$R^1$ and $R^2$, which may be same or different, respectively represent a hydrogen atom; $C_1$-$C_8$ alkyl group; phenyl group; phenyl group substituted with a substituent selected from the group consisting of halo, hydroxy, carboxy, carboalkoxy, nitro, amino, mercapto, thioalkyl, $C_1$-$C_8$ alkyl, $C_1$-$C_8$ cycloalkyl, $C_1$-$C_8$ alkoxy groups, and $C_3$-$C_8$ heterocycloalkyl group comprising at least one heteroatom selected from O and N; benzyl group; benzyl group substituted with a substituent selected from the group consisting of halo, hydroxy, carboxyl, carboalkoxy, nitro, amino, mercapto, thioalkyl, $C_1$-$C_8$ alkyl, and $C_1$-$C_8$ alkoxy groups; phenethyl group; or heteroaryl group comprising at least one heteroatom selected from O, S and N; and $R^3$ represents a hydrogen atom; $C_1$-$C_8$ alkyl group; heteroaryl group comprising at least one heteroatom selected from O, S and N; phenyl group; phenyl group substituted with a substituent selected from the group consisting of halo, hydroxy, carboxy, carboalkoxy, nitro, amino, mercapto, thioalkyl, $C_1$-$C_8$ alkyl, $C_1$-$C_8$ cycloalkyl, $C_1$-$C_8$ alkoxy groups, and $C_3$-$C_8$ heterocycloalkyl group comprising at least one heteroatom selected from O and N; benzyl group; benzyl group substituted with a substituent selected from the group consisting of halo, hydroxy, carboxy, carboalkoxy, nitro, amino, mercapto, aryl, haloaryl, $C_1$-$C_8$ alkyl, $C_1$-$C_8$ alkoxy, $C_1$-$C_8$ haloalkyl, and arylcarbonyl groups.

DETAILED DESCRIPTION OF INVENTION

The pyrazolylmethylamine-piperazine derivatives of the present invention represented by the above formula 1 can have chiral centers and these compounds may exist as racemic isomers or other possible isomers. Therefore, the present invention includes racemic isomers, every possible isomer, and mixtures thereof.

Further, the pyrazolylmethylamine-piperazine derivatives of the present invention include radioactive derivatives, and they are useful for in vivo studies.

Further, the pyrazolylmethylamine-piperazine derivatives of the present invention can form pharmaceutically acceptable salts by using the conventional methods in the art the present invention pertains to, for example, they can form pharmaceutically acceptable acid salts along with non-toxic inorganic acids such as hydrochloric acid, bromic acid, sulfonic acid, amidosulfonic acid, phosphoric acid, nitric acid, or non-toxic organic acids such as propionic acid, succinic acid, glycolic acid, stearic acid, lactic acid, tartaric acid, citric acid, p-toluenesulfonic acid, methanesulfonic acid, etc.

The substituent groups in the pyrazolylmethylamine-piperazine derivatives of the present invention represented by the above formula 1 are explained further hereinbelow.

'Alkyl' group refers to all linear, branched and cyclic carbon chains with 1-8 carbon atoms, preferably methyl, ethyl, propyl, isopropyl, butyl, isobutyl, tert-butyl, cyclopentyl, cyclohexyl groups, etc.

'Alkoxy' group refers to alkyl groups whose carbon atoms are connected to an oxygen atom, wherein 'alkyl' is the same as defined above.

'Aryl' group refers to aromatic rings comprising 6-membered ring or bicyclic entity constructed with least 10 atoms with resonance stabilization established, which includes phenyl, naphthyl groups, etc. The above aryl can be substituted with at least one substituent selected from the group consisting of halo, alkyl, alkoxy, phenoxy groups, etc.

'Benzyl' group refers to a reactive group where an aryl group is substituted with methylene and the methylene-substituted carbon atom can form a covalent bond with another atom.

'Heteroaryl' group refers to stable 5-10-membered heterocyclic entities, regardless of the degree of saturation and the shape of the ring, which comprises 1-3 heteroatoms selected from N, O, and S. The examples of the heteroaryl group includes pyridyl, imidazolyl, pyrimidyl, pyridazinyl, triazinyl, triazolyl, piperonyl, quinolinyl, isoquinolinyl, quinazolinyl, quinoxalinyl, phthalazinyl, oxazolyl, isooxazolyl, thiazolyl, isothiazolyl, thiadiazolyl, oxadiazolyl, pyrrolyl, furyl, thiophenyl groups, and their hydrogenated derivatives such as piperidinyl, pyrrolidinyl, tetrahydrofuranyl groups, and N-oxide derivatives of the basic nitrogen. The heteroaryl group can be substituted with at least one substituent selected from the group consisting of halo, alkyl, amine, alkylamino groups, etc.

'Heterocycloalkyl' group refers to cycloalkyl groups comprising 1-3 heteroatoms selected from N, O, and S, and may include piperidinyl, piperazinyl, morpholinyl groups, etc.

The pyrazolylmethylamine-piperazine derivatives represented by the above formula 1 of the present invention are selected from the pyrazolylmethylamine-piperazine compounds and their pharmaceutically acceptable salts wherein, Y represents —$(CH_2)_n$—C(O)—; or —C(O)—$(CH_2)_n$—, wherein n is an integer of 1-4, $R^1$ represents a hydrogen atom, methyl, ethyl, propyl, tert-butyl, phenyl, 4-chlorophenyl, carboxyphenyl, nitrophenyl, methoxyphenyl, fluorophenyl, dichlorophenyl, dimethylphenyl, difluorophenyl, ethylphenyl, trifluoromethylphenyl, isopropylphenyl, fluorobenzyl groups, $R^2$ represents a hydrogen atom, methyl, ethyl, propyl, isobutyl, cyclopropyl, cyclohexylmethyl, phenethyl, phenyl, methylphenyl, dimethylphenyl, trimethylphenyl, thiomethoxyphenyl, methoxyphenyl, dimethoxyphenyl, trifluoromethylphenyl, fluorophenyl, difluorophenyl, trifluorophenyl, dichlorophenyl, ethoxyphenyl, hexyloxyphenyl, trifluoromethyloxyphenyl, morpholinophenyl, piperidinophenyl, piperonyl, 1,4-benzodioxanyl, nitrophenyl, furyl, thiophenyl, benzyl, methylbenzyl, methoxybenzyl, fluorobenzyl, 4-cyclohexylphenyl, piperidinylphenyl groups, $R^3$ represents a hydrogen atom, methyl, ethyl, propyl, isobutyl, phenyl, furyl, cyclopropylcarbonyl, cyclopropyl, hydroxyphenyl, methylphenyl (2-, 3-, 4-), dimethylphenyl(2,3-, 2,4-), trimethylphenyl (2,4,6-), fluorophenyl (2-, 3-, 4-), chlorophenyl(2-, 3-, 4-), dichlorophenyl (2,3-, 2,4-), trifluorophenyl, 2-chloro-6-fluorophenyl, methoxyphenyl (2-, 3-, 4-), dimethoxyphenyl(2,3-, 2,4-), trimethoxyphenyl (2,3,4-), 4-nitrophenyl, 2-acetylphenyl, 4-acetylphenyl, 4-formylphenyl, 4-cyanophenyl, benzyl, fluorobenzyl (2-, 3-, 4-), chlorobenzyl (2-, 3-, 4-), dichlorobenzyl (2,3-, 2,4-, 3,4-), methylbenzyl (2-, 3-, 4-), dimethylbenzyl (2,3-, 2,4-), tert-butylbenzyl, trimethylbenzyl, trifluoromethylbenzyl, methoxybenzyl (2-, 3-, 4-), dimethoxybenzyl (2,3-, 2,4-), trimethoxybenzyl (2,3,4-), ethoxybenzyl, diphenylmethyl, 2-fluorophenyl(phenyl)methyl, 3-fluorophenyl(phenyl)methyl, 4-fluorophenyl(phenyl)methyl, 2,3-difluorophenyl(phenyl)methyl, 2,4-difluorophenyl(phenyl)methyl, 3,4-difluorophenyl(phenyl)methyl, 2-chlorophenyl (phenyl)methyl, 3-chlorophenyl(phenyl)methyl, 4-chlorophenyl(phenyl)methyl, 2,3-dichlorophenyl(phenyl)methyl, 2,4-dichlorophenyl(phenyl)methyl, 3,4-dichlorophenyl(phenyl)methyl, 2-methylphenyl (phenyl)methyl, 3-methylphenyl(phenyl)methyl, 4-methylphenyl(phenyl)methyl, 2,3-dimethylphenyl(phenyl)methyl, 2,4-dimethylphenyl(phenyl)methyl, 3,4-dimethylphenyl(phenyl)methyl, 2-methoxyphenyl (phenyl)methyl, 3-methoxyphenyl(phenyl)methyl, 4-methoxy(phenyl)methyl, 2,3-dimethoxyphenyl(phenyl)methyl, 2,4-dimethoxyphenyl(phenyl)methyl, 3,4-dimethoxyphenyl(phenyl)methyl, bis(2-fluorophenyl)methyl, bis(3-fluorophenyl)methyl, bis(4-fluorophenyl)methyl, bis(2,3-difluorophenyl)methyl, bis(2,4-difluorophenyl)methyl, bis(3,4-difluorophenyl)methyl, bis(2-chlorophenyl)methyl, bis(3-chlorophenyl)methyl, bis(4-chlorophenyl)methyl, bis(2,3-dichlorophenyl)methyl, bis(2,4-dichlorophenyl)methyl, bis(3,4-dichlorophenyl)methyl, bis(2-methylphenyl)methyl, bis(3-methylphenyl)methyl, bis(4-methylphenyl)methyl, bis(2,3-dimethylphenyl)methyl, bis(2,4-dimethylphenyl)methyl, bis(3,4-dimethylphenyl)methyl, bis(2-methoxyphenyl)methyl, bis(3-methoxyphenyl)methyl, bis(4-methoxyphenyl)methyl, bis(2,3-dimethoxyphenyl)methyl, bis(2,4-dimethoxyphenyl)methyl, bis(3,4-dimethoxyphenyl)methyl, piperonyl, pyridyl, pyrimidyl, furanoyl groups.

The pyrazolylmethylamine-piperazine derivatives represented by the above formula 1 of the present invention are selected from the pyrazolylmethylamine-piperazine compounds and their pharmaceutically acceptable salts wherein, preferably, Y represents —$(CH_2)_n$—C(O)—; or —C(O)—$(CH_2)_n$—, wherein n is an integer of 1-4;

$R^1$ and $R^2$, which may be same or different, respectively represent a hydrogen atom; $C_1$-$C_8$ alkyl; phenyl; benzyl; phenethyl; or heteroaryl groups;

$R^3$ represents phenyl; benzyl; benzhydryl; benzoyl; heteroaryl; or heteroarylcarbonyl groups;

wherein the phenyl, benzyl, benzhydryl, benzoyl, heteroaryl, or heteroarylcarbonyl groups in $R^1$, $R^2$, and $R^3$ can be respectively substituted with 1-3 substituents selected from the group consisting of halo, hydroxy, nitro, cyano, carboxyl, $C_1$-$C_8$ alkyl, $C_1$-$C_8$ haloalkyl, $C_1$-$C_8$ thioalkyl, $C_1$-$C_8$ alkoxy groups, and 5-7 membered heterocycloalkyl groups comprising at least one heteroatom selected from O, S and N;

wherein the heteroaryl or heterocycloalkyl groups represent 5-10 membered monocyclic or fused rings comprising at least one heteroatom selected from O, S, and N.

The pyrazolylmethylamine-piperazine derivatives represented by the above formula 1 of the present invention are selected from the pyrazolylmethylamine-piperazine compounds and their pharmaceutically acceptable salts wherein, more preferably, Y represents —$CH_2$—C(O)—; or —C(O)—$CH_2$—;

$R^1$ represents a hydrogen atom, phenyl, carboxylphenyl, $C_1$-$C_8$ alkoxyphenyl, or benzyl groups;

$R^2$ represents $C_1$-$C_8$ alkyl group; phenyl group; phenyl group substituted with 1-3 substituents selected from the group consisting of $C_1$-$C_8$ alkyl, $C_1$-$C_8$ thioalkyl, $C_1$-$C_8$ alkoxy, piperidinyl and morpholinyl groups; phenethyl; furyl group; or pyridyl group; and $R^3$ represents phenyl; phenyl substituted with 1-3 substituents selected from the group consisting of hydroxy, cyano and $C_1$-$C_8$ alkyl groups; benzyl group; benzyl group substituted with 1-3 substituents selected from the group consisting of phenyl, benzyl, halo, $C_1$-$C_8$ alkyl, $C_1$-$C_8$ haloalkyl, and $C_1$-$C_8$ alkoxy groups; heteroaryl group selected from the group consisting of furyl, pyridyl, pyrimidyl, and piperonyl groups; benzhydryl group; benzhydryl group substituted with halogen; or furanoyl group.

The pyrazolylmethylamine-piperazine derivatives represented by the above formula 1 of the present invention are selected from the pyrazolylmethylamine-piperazine compounds and their pharmaceutically acceptable salts wherein, most preferably, Y represents —$CH_2$—C(O)—, or —C(O)—$CH_2$—;

$R^1$ represents a hydrogen atom, phenyl, carboxyphenyl, methoxyphenyl, or benzyl group;

$R^2$ represents methyl, ethyl, n-propyl, isopropyl, isobutyl, tert-butyl, phenyl, toluyl, methoxyphenyl, thiomethylphenyl, morpholinophenyl, piperidinophenyl, phenethyl, furyl, or pyridyl group; and $R^3$ represents phenyl, hydroxyphenyl, cyanophenyl, dimethylphenyl, benzyl, halobenzyl, dihalobenzyl, methylbenzyl, dimethylbenzyl, trimethylbenzyl, trifluoromethylbenzyl, trimethoxybenzyl, benzhydryl, (halolphenyl)(phenyl)methyl, pyridyl, pyrimidyl, piperonyl, or furanoyl group.

Examples of pyrazolylmethylamine-piperazine derivatives represented by the above formula 1 are as follows:

3-{[4-(2,3-dimethyl)phenylpiperazin-1-yl]methylcarboxamido}methyl-5-methyl-1-phenyl-1H-pyrazole (Compound No. 1)

3-[(4-phenylpiperazin-1-yl)methylcarboxamido]methyl-5-methyl-1-phenyl-1H-pyrazole (Compound No. 2)

3-[(4-benzhydrylpiperazin-1-yl)methylcarboxamido]methyl-5-methyl-1-phenyl-1H-pyrazole (Compound No. 3)

3-{[4-(2,4-dimethylphenyl)piperazin-1-yl]methylcarboxamido}methyl-5-methyl-1-phenyl-1H-pyrazole (Compound No. 4)

3-{[4-(3-trifluoromethyl)benzylpiperazin-1-yl]methylcarboxamido}methyl-5-methyl-1-phenyl-1H-pyrazole (Compound No. 5)

3-{[4-(3,4-dichlorobenzyl)piperazin-1-yl]methylcarboxamido}methyl-5-methyl-1-phenyl-1H-pyrazole (Compound No. 6)

3-{[4-trifluoromethyl)benzylpiperazin-1-yl]methylcarboxamido}methyl-5-methyl-1-phenyl-1H-pyrazole (Compound No. 7)

3-{[4-(2,3,4-trimethoxy)benzylpiperazin-1-yl]methylcarboxamido}methyl-5-methyl-1-phenyl-1H-pyrazole (Compound No. 8)

3-[(4-phenylpiperazin-1-yl)methylcarboxamido]methyl-5-isobutyl-1-phenyl-1H-pyrazole (Compound No. 9)

3-{[4-(2,3-dimethylphenyl)piperazin-1-yl]methylcarboxamido}methyl-5-isobutyl-1-phenyl-1H-pyrazole (Compound No. 10)

3-[(4-phenylpiperazin-1-yl)methylcarboxamido]methyl-5-furyl-1-phenyl-1H-pyrazole (Compound No. 11)

3-{[4-(2,3-dimethylphenyl)piperazin-1-yl]methylcarboxamido}methyl-5-furyl-1-phenyl-1H-pyrazole (Compound No. 12)

3-{[4-(3-trifluoromethylbenzyl)piperazin-1-yl]methylcarboxamido}methyl-5-furyl-1-phenyl-1H-pyrazole (Compound No. 13)

3-{[4-(4-trifluoromethylbenzyl)piperazin-1-yl]methylcarboxamido}methyl-5-furyl-1-phenyl-1H-pyrazole (Compound No. 14)

3-{[4-(3-trifluoromethylbenzyl)piperazin-1-yl]methylcarboxamido}methyl-5-isobutyl-1-phenyl-1H-pyrazole (Compound No. 15)

3-{[4-(4-trifluoromethylbenzyl)piperazin-1-yl]methylcarboxamido}methyl-5-isobutyl-1-phenyl-1H-pyrazole (Compound No. 16)

3-{[4-(2,3,4-trimethoxy)benzylpiperazin-1-yl]methylcarboxamido}methyl-5-isobutyl-1-phenyl-1H-pyrazole (Compound No. 17)

3-{[4-(2,3,4-trimethoxy)benzylpiperazin-1-yl]methylcarboxamido}methyl-5-furyl-1-phenyl-1H-pyrazole (Compound No. 18)

3-[(4-benzhydrylpiperazin-1-yl)methylcarboxamido]methyl-5-isobutyl-1-phenyl-1H-pyrazole (Compound No. 19)

3-[(4-benzhydrylpiperazin-1-yl)methylcarboxamido]methyl-5-furyl-1-phenyl-1H-pyrazole (Compound No. 20)

3-[(4-piperonylpiperazin-1-yl)methylcarboxamido]methyl-5-isobutyl-1-phenyl-1H-pyrazole (Compound No. 21)

3-[(4-piperonylpiperazin-1-yl)methylcarboxamido]methyl-5-furyl-1-phenyl-1H-pyrazole (Compound No. 22)

3-{[4-(3,4-dichloro)benzylpiperazin-1-yl]methylcarboxamido}methyl-5-furyl-1-phenyl-1H-pyrazole (Compound No. 23)

3-{[4-(3,4-dichloro)benzylpiperazin-1-yl]methylcarboxamido}methyl-5-isobutyl-1-phenyl-1H-pyrazole (Compound No. 24)

3-{[4-(4-chlorophenyl)(phenyl)methylpiperazin-1-yl]methylcarboxamido}methyl-5-methyl-1-phenyl-1H-pyrazole (Compound No. 25)

3-{[4-(4-chlorophenyl)(phenyl)methylpiperazin-1-yl]methylcarboxamido}methyl-5-furyl-1-phenyl-1H-pyrazole (Compound No. 26)

3-[(4-phenylpiperazin-1-yl)methylcarboxamido]methyl-5-propyl-1-phenyl-1H-pyrazole (Compound No. 27)

3-{[4-(2,3-dimethyl)phenylpiperazin-1-yl]methylcarboxamido}methyl-5-propyl-1-phenyl-1H-pyrazole (Compound No. 28)

3-{[4-(2,4-dimethyl)phenylpiperazin-1-yl]methylcarboxamido}methyl-5-propyl-1-phenyl-1H-pyrazole (Compound No. 29)

3-[(4-benzhydrylpiperazin-1-yl)methylcarboxamido]methyl-5-propyl-1-phenyl-1H-pyrazole (Compound No. 30)

3-{[4-(3-trifluoromethyl)benzylpiperazin-1-yl]methylcarboxamido}methyl-5-propyl-1-phenyl-1H-pyrazole (Compound No. 31)

3-{[4-(4-trifluoromethyl)benzylpiperazin-1-yl]methylcarboxamido}methyl-5-propyl-1-phenyl-1H-pyrazole (Compound No. 32)

3-[(4-piperonylpiperazin-1-yl)methylcarboxamido]methyl-5-propyl-1-phenyl-1H-pyrazole (Compound No. 33)

3-{[4-(2-pyridyl)piperazin-1-yl]methylcarboxamido}methyl-5-methyl-1-phenyl-1H-pyrazole (Compound No. 34) 3-{[4-(2-pyrimidyl)piperazin-1-yl]methylcarboxamido}methyl-5-methyl-1-phenyl-1H-pyrazole (Compound No. 35)

3-{[4-(2-pyridyl)piperazin-1-yl]methylcarboxamido}methyl-5-isobutyl-1-phenyl-1H-pyrazole (Compound No. 36)

3-{[4-(2-pyrimidyl)piperazin-1-yl]methylcarboxamido}methyl-5-isobutyl-1-phenyl-1H-pyrazole (Compound No. 37)

3-{[4-(2-(pyridyl)piperazin-1-yl]methylcarboxamido}methyl-5-furyl-1-phenyl-1H-pyrazole (Compound No. 38)

3-{[4-(2-pyrimidyl)piperazin-1-yl]methylcarboxamido}methyl-5-furyl-1-phenyl-1H-pyrazole (Compound No. 39)

3-{[4-(4-t-butyl)benzylpiperazin-1-yl]methylcarboxamido}methyl-5-methyl-1-phenyl-1H-pyrazole (Compound No. 40)

3-{[4-(2,4,6-trimethyl)benzylpiperazin-1-yl]methylcarboxamido}methyl-5-methyl-1-phenyl-1H-pyrazole (Compound No. 41)

3-{[4-(4-t-butyl)benzylpiperazin-1-yl]methylcarboxamido}methyl-5-isobutyl-1-phenyl-1H-pyrazole (Compound No. 42)

3-{[4-(2,4,6-trimethyl)benzylpiperazin-1-yl]methylcarboxamido}methyl-5-isobutyl-1-phenyl-1H-pyrazole (Compound No. 43)

3-{[4-(2,3-dimethylphenyl)piperazin-1-yl]methylcarboxamido}methyl-5-(4-methoxy)phenyl-1-phenyl-1H-pyrazole (Compound No. 44)

3-{[4-(2,4-dimethylphenyl)piperazin-1-yl]methylcarboxamido}methyl-5-(4-methoxy)phenyl-1-phenyl-1H-pyrazole (Compound No. 45)

3-[(4-furoylpiperazin-1-yl)methylcarboxamido]methyl-5-methyl-1-phenyl-1H-pyrazole (Compound No. 46)

3-[(4-furoylpiperazin-1-yl)methylcarboxamido]methyl-5-isobutyl-1-phenyl-1H-pyrazole (Compound No. 47)

3-{[4-(2-cyanophenyl)piperazin-1-yl]methylcarboxamido}methyl-5-methyl-1-phenyl-1H-pyrazole (Compound No. 48)

3-{[4-(2-cyanophenyl)piperazin-1-yl]methylcarboxamido}methyl-5-propyl-1-phenyl-1H-pyrazole (Compound No. 49)

3-{[4-(2,3-dimethylphenyl)piperazin-1-yl]methylcarboxamido}methyl-5-(4-thiomethyl)phenyl-1-phenyl-1H-pyrazole (Compound No. 50)

3-{[4-(2,4-dimethylphenyl)piperazin-1-yl]methylcarboxamido}methyl-5-(4-thiomethyl)phenyl-1-phenyl-1H-pyrazole (Compound No. 51)

3-{[4-(3-hydroxyphenyl)piperazin-1-yl]methylcarboxamido}methyl-5-methyl-1-phenyl-1H-pyrazole (Compound No. 52)

3-{[4-(3-hydroxyphenyl)piperazin-1-yl]methylcarboxamido}methyl-5-isobutyl-1-phenyl-1H-pyrazole (Compound No. 53)

3-[(4-phenylpiperazin-1-yl)methylcarboxamido]methyl-5-(4-thiomethyl)phenyl-1-phenyl-1H-pyrazole (Compound No. 54)

3-{[4-(3-hydroxyphenyl)piperazin-1-yl]methylcarboxamido}methyl-5-(4-thiomethyl)phenyl-1-phenyl-1H-pyrazole (Compound No. 55)

3-{[4-(2,3-dimethylphenyl)piperazin-1-yl]methylcarboxamido}methyl-5-propyl-1-(4-carboxyl)phenyl-1H-pyrazole (Compound No. 56)

3-{[4-(2,3-dimethylphenyl)piperazin-1-yl]methylcarboxamido}methyl-5-isobutyl-1-(4-carboxyl)phenyl-1H-pyrazole (Compound No. 57)

3-{[4-(2,3-dimethylphenyl)piperazin-1-yl]methylcarboxamido}methyl-5-methyl-1-(4-carboxyl)phenyl-1H-pyrazole (Compound No. 58)

3-{[4-(2,3-dimethylphenyl)piperazin-1-yl]methylcarboxamido}methyl-5-(4-morpholino)phenyl-1-phenyl-1H-pyrazole (Compound No. 59)

3-[(4-phenylpiperazin-1-yl)methylcarboxamido]methyl-5-(4-morpholino)phenyl-1-phenyl-1H-pyrazole (Compound No. 60)

3-{[4-(2,4-dimethylphenyl)piperazin-1-yl]methylcarboxamido}methyl-5-(4-morpholino)phenyl-1-phenyl-1H-pyrazole (Compound No. 61)

3-{[4-(3-trifluorobenzyl)piperazin-1-yl]methylcarboxamido}methyl-5-(4-morpholino)phenyl-1-phenyl-1H-pyrazole (Compound No. 62)

3-{[4-(4-trifluorobenzyl)piperazin-1-yl]methylcarboxamido}methyl-5-(4-morpholino)phenyl-1-phenyl-1H-pyrazole (Compound No. 63)

3-{[4-(2,3-dimethylphenyl)piperazin-1-yl]carbonylmethylamino}methyl-5-methyl-1-phenyl-1H-pyrazole (Compound No. 64)

3-[(4-benzhydrylpiperazin-1-yl)carbonylmethylamino]methyl-5-methyl-1-phenyl-1H-pyrazole (Compound No. 65)

3-[(4-phenylpiperazin-1-yl)carbonylmethylamino]methyl-5-methyl-1-phenyl-1H-pyrazole (Compound No. 66)

3-[(4-phenylpiperazin-1-yl)carbonylmethylamino]methyl-5-isobutyl-1-phenyl-1H-pyrazole (Compound No. 67)

3-[(4-benzhydrylpiperazin-1-yl)carbonylmethylamino]methyl-5-isobutyl-1-phenyl-1H-pyrazole (Compound No. 68)

3-{[4-(2,4-dimethylphenyl)piperazin-1-yl]carbonylmethylamino}methyl-5-isobutyl-1-phenyl-1H-pyrazole (Compound No. 69)

3-[(4-phenylpiperazin-1-yl)carbonylmethylamino]methyl-5-furyl-1-phenyl-1H-pyrazole (Compound No. 70)

3-[(4-benzhydrylpiperazin-1-yl)carbonylmethylamino]methyl-5-furyl-1-phenyl-1H-pyrazole (Compound No. 71)

3-{[4-(2,4-dimethyl)phenylpiperazin-1-yl]carbonylmethylamino}methyl-5-furyl-1-phenyl-1H-pyrazole (Compound No. 72)

3-{[4-(2,4-dimethyl)phenylpiperazin-1-yl]carbonylmethylamino}methyl-5-methyl-1-phenyl-1H-pyrazole (Compound No. 73)

3-{[4-(3,4-dichloro)benzylpiperazin-1-yl]carbonylmethylamino}methyl-5-methyl-1-phenyl-1H-pyrazole (Compound No. 74)

3-{[4-(3,4-dichlorobenzyl)piperazin-1-yl]carbonylmethylamino}methyl-5-isobutyl-1-phenyl-1H-pyrazole (Compound No. 75)

3-{[4-(2,3-dimethylphenyl)piperazin-1-yl]carbonylmethylamino}methyl-5-isobutyl-1-phenyl-1H-pyrazole (Compound No. 76)

3-{[4-(2,3-dimethylphenyl)piperazin-1-yl]carbonylmethylamino}methyl-5-furyl-1-phenyl-1H-pyrazole (Compound No. 77)

3-{[4-(3,4-dichlorobenzyl)piperazin-1-yl]carbonylmethylamino}methyl-5-furyl-1-phenyl-1H-pyrazole (Compound No. 78)

3-[(4-piperonylpiperazin-1-yl)carbonylmethylamino]methyl-5-isobutyl-1-phenyl-1H-pyrazole (Compound No. 79)

3-[(4-piperonylpiperazin-1-yl)carbonylmethylamino]methyl-5-furyl-1-phenyl-1H-pyrazole (Compound No. 80)

3-{[4-(2,3,4-trimethoxybenzyl)piperazin-1-yl]carbonylmethylamino}methyl-5-isobutyl-1-phenyl-1H-pyrazole (Compound No. 81)

3-{[4-(2,3-dimethylphenyl)piperazin-1-yl]carbonylmethylamino}methyl-5-propyl-1-phenyl-1H-pyrazole (Compound No. 82)

3-{[4-(2,4-dimethylphenyl)piperazin-1-yl]carbonylmethylamino}methyl-5-propyl-1-phenyl-1H-pyrazole (Compound No. 83)

3-[(4-phenylpiperazin-1-yl)carbonylmethylamino]methyl-5-propyl-1-phenyl-1H-pyrazole (Compound No. 84)

3-[(4-phenylpiperazin-1-yl)methylcarboxamido]methyl-5-methyl-1-[(4-methoxy)phenyl]-1H-pyrazole (Compound No. 85)

3-[(4-phenylpiperazin-1-yl)methylcarboxamido]methyl-5-[(4-piperidino)phenyl]-1-phenyl-1H-pyrazole (Compound No. 86)

3-[(4-phenylpiperazin-1-yl)methylcarboxamido]methyl-5-isobutyl-1-[(4-methoxy)phenyl]-1H-pyrazole (Compound No. 87)

3-{(4-(2,3-dimethylphenyl)piperazin-1-yl]methylcarboxamido}methyl-5-isobutyl-1-[(4-methoxy)phenyl]-1H-pyrazole (Compound No. 88)

3-[(4-phenylpiperazin-1-yl)methylcarboxamido]methyl-5-(2-pyridyl)-1-phenyl-1H-pyrazole (Compound No. 89)

3-{(4-(2,3-dimethylphenyl)piperazin-1-yl]methylcarboxamido}methyl-5-(2-pyridyl)-1-phenyl-1H-pyrazole (Compound No. 90)

3-[(4-phenylpiperazin-1-yl)methylcarboxamido]methyl-5-[(4-methyl)phenyl]-1-phenyl-1H-pyrazole (Compound No. 91)

3-{(4-(2,3-dimethylphenyl)piperazin-1-yl]methylcarboxamido}methyl-5-[(4-methyl)phenyl]-1-phenyl-1H-pyrazole (Compound No. 92)

3-[(4-phenylpiperazin-1-yl)methylcarboxamido]methyl-5-methyl-1-benzyl-1H-pyrazole (Compound No. 93)

3-{(4-(2,3-dimethylphenyl)piperazin-1-yl]methylcarboxamido}methyl-5-methyl-1-benzyl-1H-pyrazole (Compound No. 94)

3-{[4-(2,3-dimethylphenyl)piperazin-1-yl]carbonylmethylamino}methyl-5-methyl-1H-pyrazole (Compound No. 95)

The present invention also relates to preparation methods of pyrazolylmethylamine-piperazine derivatives represented by the above formula 1 of the present invention.

One of the preparation methods of pyrazolylmethylamine-piperazine derivatives wherein Y is —C(O)—$CH_2$—, is to perform a coupling reaction between a haloacetylpiperazine compound represented by the formula 2 and a pyrazolylmethylamine compound represented by the formula 3 in the Reaction Scheme 1 below;

[Reaction Scheme 1]

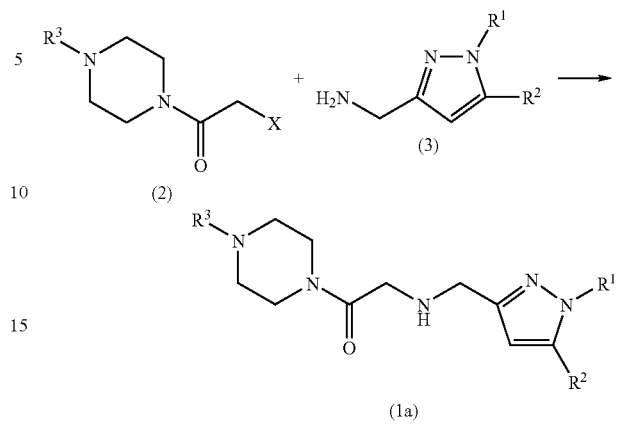

wherein $R^1$, $R^2$, and $R^3$ are respectively the same as defined above and X represents a halogen atom.

Another preparation method of pyrazolylmethylamine-piperazine derivatives wherein Y is —$CH_2$—C(O)—, is to perform a coupling reaction between a piperazine compound represented by the formula 4 and a pyrazolylmethylcarbamoylmethyl halide compound represented by the formula 5 in the Reaction Scheme 2 below;

[Reaction Scheme 2]

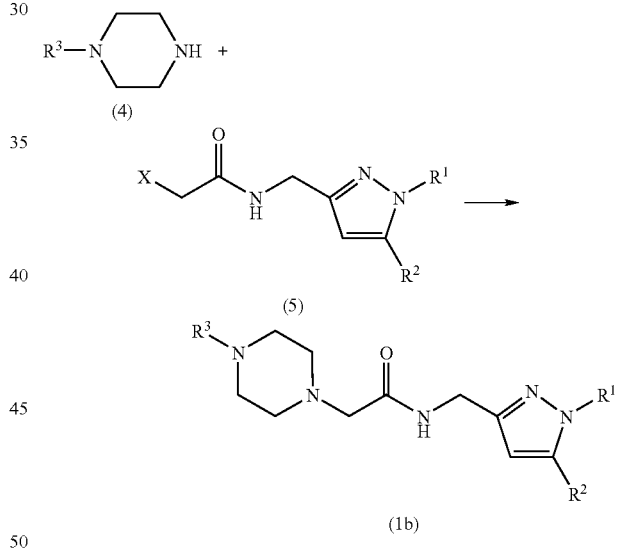

wherein, $R^1$, $R^2$, and $R^3$ are respectively the same as defined above and X represents a halogen atom.

The above reaction schemes 1 and 2 can be performed under the conditions of using a suitable base and an organic solvent.

Examples of the bases include carbonates and sulfates of alkaline metals or alkaline earth metals, inorganic bases such as hydroxide, or organic bases such as mono($C_1$-$C_5$ alkyl)amine, di($C_1$-$C_5$ alkyl)amine, etc.

Examples of the solvents include organic solvents conventionally used in the art the present invention pertains to, such as inert organic solvents. More specifically, examples of the organic solvents to be used in the present invention are diethyl ether; $C_1$-$C_6$ primary alcohols such as methanol, ethanol, propanol; tetrahydrofuran; halogenated compounds such as chloroform, methylene chloride; nitrile compounds such as acetonitrile, etc.

The reaction can be performed at a temperature between −30° C. and a reflux temperature of the solvent used, preferably between room temperature and 120° C., more preferably between 30° C. and 80° C.

The haloacetylpiperazine compound used as a starting material of the present invention represented by the above formula 2 can be manufactured by reacting a piperazine compound represented by the formula 4 below with a haloacetyl halide represented by the formula 6 below;

[Reaction Scheme 3]

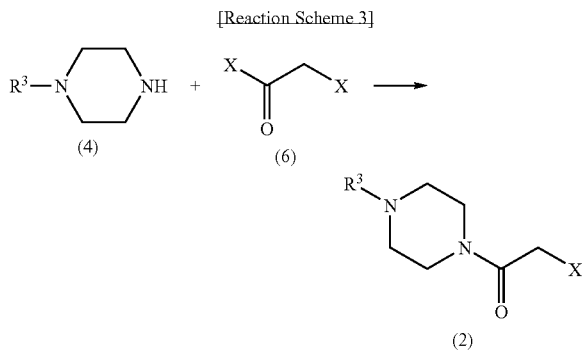

wherein, in the above Reaction Scheme 3, $R^3$ is the same as defined above, and X represents a halogen atom.

Further, the pyrazolylmethylcarbamoylmethyl halide compound, used as a starting material represented by the above formula 5 is a novel compound, and the present invention includes the pyrazolylmethylcarbamoylmethyl halide compound as a novel intermediate compound and its manufacturing method within the claim scope.

A method of manufacturing the novel intermediate compound, pyrazolylmethylcarbamoylmethyl halide compound represented by the above formula 5, comprises:

(1) converting a pyrazolaldehyde compound represented by the formula 7 below to a pyrazoloxime compound represented by the formula 8 below;

(2) converting said pyrazoloxime compound represented by the formula 8 below to a pyrazolylamine compound represented by the formula 9 below; and (3) converting said pyrazolylamine compound represented by the formula 9 below to a pyrazolylmethylcarbamoylmethyl halide compound represented by the formula 5 below:

[Reaction Scheme 4]

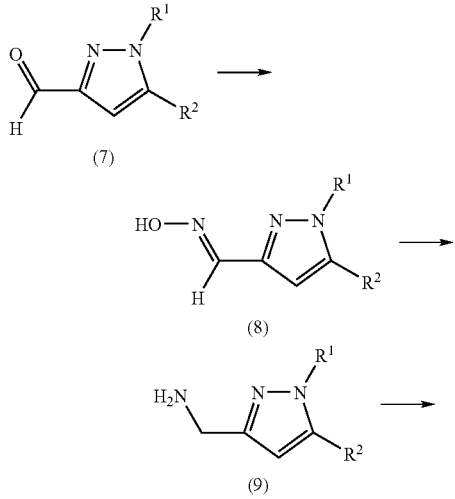

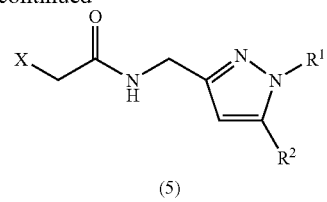

wherein, in the above Reaction Scheme 4, $R^1$ and $R^2$ are respectively the same as defined above, and X represents a halogen atom.

The preparation of pyrazoloxime compound represented by the above formula 8 is achieved by reacting the pyrazolaldehyde compound represented by the above formula 7, which is obtained by the reduction of a pyrazole ester compound, with hydroxylamine HCl in the presence of a base.

The preparation of pyrazolamine compound represented by the above formula 9 is achieved by reducing the pyrazoloxime compound represented by the above formula 8.

Examples of reducing agents include inorganic catalysts which are involved in hydrogenation, or other commercially available various metal hydrides, preferably lithium aluminum hydride.

The preparation of pyrazolylmethylcarbamoylmethyl halide compound represented by the above formula 5 is achieved by performing a coupling reaction of the pyrazolamine compound represented by the above formula 9 with a haloacetyl halide represented by the above formula 6.

The solvent used in the above reaction scheme 4 may include, without limitation, any conventional inert organic solvent which does not affect the reaction. More specifically, the organic solvents to be used in the present invention include diethyl ether; $C_1$-$C_6$ primary alcohols such as methanol, ethanol, propanol; tetrahydrofuran; halogenated compounds such as chloroform, methylene chloride; nitrile compounds such as acetonitrile, etc.

The reaction can be performed at a temperature between −30° C. and a reflux temperature of the solvent used, preferably between room temperature and 120° C., more preferably between 30° C. and 80° C.

Meanwhile, considering that the pyrazolylmethylamine-piperazine derivatives represented by the formula 1 and their pharmaceutically acceptable salts are very effective as T-type calcium channel antagonists, the present invention includes pharmaceutical compositions comprising the novel compound represented by the formula 1 within the scope of the claim.

Further, the pharmaceutical compositions of the present invention which comprise pyrazolylmethylamine-piperazine derivatives and their pharmaceutically acceptable salts as active ingredients thus are useful for the prevention and treatment of diseases by their antagonistic activities against T-type calcium channels.

Examples of the diseases to be treated by antagonizing the T-type calcium channel include cancers; diabetes; obesity; cerebral diseases such as epilepsy, depression, Parkinson's disease, dementia, sleep disorder; cardiovascular diseases such as hypertension, cardiac arrhythmia, angina pectoris, myocardial infarction and congestive heart failure; and pain-related diseases such as neuropathic pain, chronic and acute pains.

The pharmaceutical compositions of the present invention can be formulated into oral or parenteral preparations in the form of tablets, capsules, troches, liquids, suspensions by adding conventional pharmaceutically acceptable non-toxic additives such as a carrier, a reinforcing agent, and an excipient to the compound represented by the above formula 1.

Further, the dosage of the compound represented by the above formula 1 can vary depending on the age, body weight, sex, type of administration, health conditions, severeness of disease of patients. For an adult with 70 kg of body weight, in general, 0.01-400 mg/day of dosage is given and it may be administered once daily or a few times a day at regular intervals as per the physician's prescription.

As stated above, the present invention is described more specifically with reference to the following Reference Synthesis Examples and Examples. However, it should not be construed as limiting the scope of the present invention.

REFERENCE SYNTHESIS EXAMPLES

Reference Synthesis Example 1

Synthesis of 3-formyl-5-methyl-1-phenylpyrazole

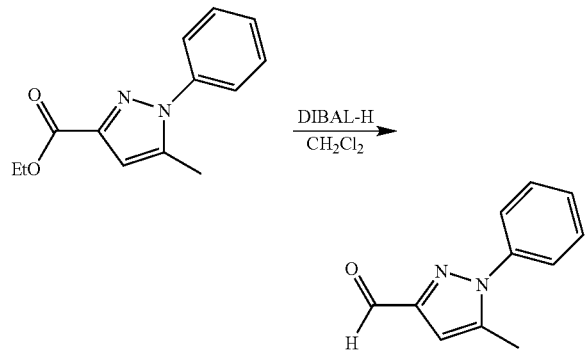

3-Ethoxycarbonyl-1-phenyl-5-methylpyrazole (3.482 g, 15.12 mmol) was dissolved in 20 mL of purified methylene chloride, and then dropwisely added with DIBAL (45.36 mL, 45.36 mmol) at −78° C. and stirred. Termination of the reaction was confirmed by TLC (hexane:ethyl acetate=5:1). Upon completion of reaction, the reaction mixture was dropwisely added with methanol and water, and then extracted with methylene chloride. The resulting organic layer was dried with anhydrous magnesium sulfate and filtered, and the filtrate was concentrated and dried in vacuo to obtain the target compound, 3-formyl-5-methyl-1-phenylpyrazole.

Yield: 81.7%

$^1$H NMR (300 MHz, CDCl$_3$) δ 9.94 (s, 1H), 7.37-7.49 (m, 5H), 6.66 (s, 1H), 2.28 (s, 3H)

Reference Synthesis Example 2

Synthesis of 3-formyl-5-isobutyl-1-phenylpyrazole

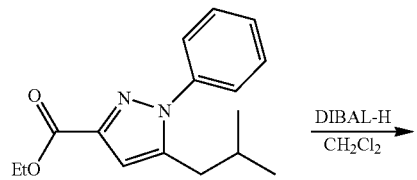

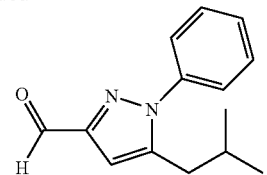

3-Formyl-5-isobutyl-1-phenylpyrazole was obtained by using the manufacturing method same as in the above Reference Example 1.

Yield: 99.0%

$^1$H NMR (300 MHz, CDCl$_3$) δ 10.01 (s, 1H), 7.50-7.55 (m, 3H), 7.42-7.48 (m, 2H), 6.75 (s, 1H), 2.54 (t, J=7.20, 2H), 1.83-1.88 (m, 1H), 0.89 (s, 3H), 0.87 (s, 3H)

Reference Synthesis Example 3

Synthesis of 3-formyl-5-furyl-1-phenylpyrazole

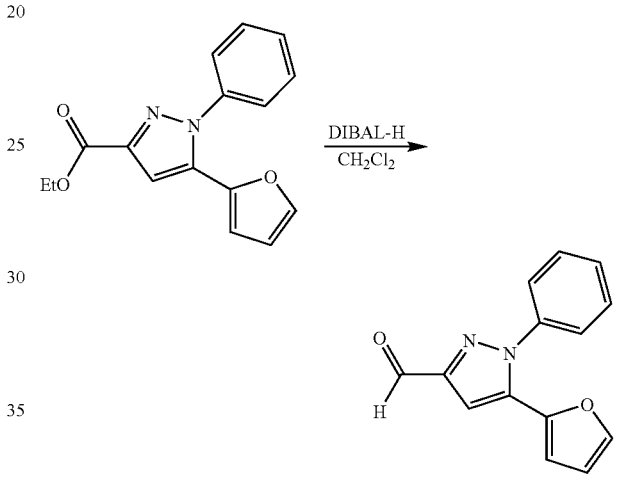

3-Formyl-5-furyl-1-phenylpyrazole was obtained by using the manufacturing method same as in the above Reference Example 1.

Yield: 92.1%

$^1$H NMR (300 MHz, CDCl$_3$) δ 10.06 (s, 1H), 7.44-7.55 (m, 6H), 7.16 (s, 1H), 6.35-6.36 (m, 1H), 6.00 (d, J=3.45, 1H)

Pyrazole aldehyde compounds with various substituents at the C1 and C5 positions were obtained by using the preparation method same as in the above Reference Example 1.

EXAMPLES

Example 1

Synthesis of 5-methyl-1-phenylpyrazole-3-oxime

NH$_2$OH.HCl (1.272 g, 18.31 mmol) and triethylamine (2.55 mL, 18.31 mmol) were dissolved in 20 mL of purified methylene chloride, and stirred under nitrogen atmosphere. When the mixture reached pH 7, it was dropwisely added with 3-formyl-5-methyl-1-phenylpyrazole (2.273 g, 12.21 mmol), which was prepared in the reference synthesis example, and stirred at room temperature. Termination of the reaction was confirmed by TLC (hexane:ethyl acetate=1:1). Upon completion of reaction, the reaction mixture was extracted with methylene chloride. The resulting organic layer was dried with anhydrous magnesium sulfate and filtered, and the filtrate was concentrated and dried in vacuo to obtain the title compound.

Yield: 91.6%

$^1$H NMR (300 MHz, CDCl$_3$) δ 8.07 (s, 1H), 7.42-7.55 (m, 5H), 7.03 (s, 1H), 6.55 (s, 1H), 2.29 (s, 3H)

Example 2

Synthesis of 5-isobutyl-1-phenylpyrazole-3-oxime

Title compound was obtained by using the manufacturing method same as in the above Example 1.

Yield: 92.5%

$^1$H NMR (300 MHz, CDCl$_3$) δ 8.10 (s, 1H), 7.40-7.55 (m, 5H), 6.60 (s, 1H), 2.53 (d, J=7.09 Hz, 2H), 1.73-1.82 (m, 1H), 0.84 (s, 3H), 0.82 (s, 3H)

Example 3

Synthesis of 5-furyl-1-phenylpyrazole-3-oxime

Title compound was obtained by using the manufacturing method same as in the above Example 1.

Yield: 96.3%

$^1$H NMR (300 MHz, CDCl$_3$) δ 8.26 (s, 1H), 7.68 (s, 1H), 7.41-7.51 (m, 5H), 7.30 (s, 1H), 6.34-6.35 (m, 1H), 5.99-6.00 (m, 1H)

Example 4

Synthesis of 5-methyl-3-aminomethyl-1-phenylpyrazole

5-Methyl-1-phenylpyrazole-3-oxime (1.771 g, 8.80 mmol) was dissolved in 20 mL of purified diethyl ether, dropwisely added with LAH (22.9 mL, 22.9 mmol) suspension in diethyl ether under nitrogen atmosphere at 0° C., and stirred at room temperature. Termination of the reaction was confirmed by TLC (hexane:ethyl acetate=1:1). Upon completion of reaction, the reaction mixture was dropwisely added with NaOH and water, and the resulting solid was filtered. The filtrate was extracted with methylene chloride. The resulting organic layer was dried with anhydrous magnesium sulfate and filtered, and the filtrate was concentrated and dried in vacuo to obtain the title compound.

Yield: 75.5%

$^1$H NMR (300 MHz, CDCl$_3$) δ 7.23-7.28 (m, 5H), 5.97 (s, 1H), 3.75 (s, 2H), 2.13 (s, 3H)

Example 5

Synthesis of 5-isobutyl-3-aminomethyl-1-phenylpyrazole

Title compound was obtained by using the manufacturing method same as in the above Example 4.

Yield: 80.9%

$^1$H NMR (300 MHz, CDCl$_3$) δ 7.37-7.48 (m, 5H), 6.14 (s, 1H), 3.91 (s, 2H), 2.49 (d, J=7.17 Hz, 2H), 1.79-1.84 (m, 1H), 0.97 (m, 3H), 0.84 (s, 3H)

Example 6

Synthesis of 5-furyl-3-aminomethyl-1-phenylpyrazole

Title compound was obtained by using the manufacturing method same as in the above Example 4.

Yield: 79.9%

$^1$H NMR (300 MHz, CDCl$_3$) δ 7.37-7.41 (m, 5H), 6.59 (s, 1H), 6.30-6.31 (m, 1H), 5.95 (d, J=3.27 Hz, 1H), 3.94 (s, 2H), 2.34 (br, 2H)

Example 7

Synthesis of 3-(2-chloroacetamido)methyl-1-phenyl-5-methylpyrazole

5-Methyl-3-aminomethyl-1-phenylpyrazole (2.434 g, 15 mmol) was dissolved in 20 mL of purified methylene chloride, dropwisely added with chloroacetyl chloride (1.194 mL, 15 mmol) at 0° C. and then stirred at room temperature. Completion of the reaction was confirmed by TLC (hexane:ethyl acetate=1:1). Upon completion of reaction, the reaction mixture was adjusted to pH 7 using saturated aq. NaHCO$_3$ and then extracted with methylene chloride. The resulting organic layer was dried with anhydrous magnesium sulfate and filtered, and the filtrate was concentrated and dried in vacuo to obtain the title compound, 3-(2-chloroacetamido)methyl-1-phenyl-5-methylpyrazole.

Yield: 60.8%

$^1$H NMR (300 MHz, CDCl$_3$) δ 7.57 (br, 1H), 7.34-7.46 (m, 5H), 6.19 (s, 1H), 4.48 (d, J=5.49 Hz, 2H), 3.96 (s, 2H), 2.26 (s, 3H)

Example 8

Synthesis of 3-(2-chloroacetamido)methyl-1-phenyl-5-isobutylpyrazole

Title compound was obtained by using the manufacturing method same as in the above Example 7.

Yield: 46.1%

$^1$H NMR (300 MHz, CDCl$_3$) δ 7.36-7.49 (m, 5H), 7.12 (br, 1H), 6.15 (s, 1H), 4.52 (d, J=5.37 Hz, 2H), 4.07 (s, 2H), 2.49 (d, J=7.17 Hz, 2H), 1.79-1.83 (m, 1H), 0.86 (s, 3H), 0.84 (s, 3H)

Example 9

Synthesis of 3-(2-chloroacetamido)methyl-1-phenyl-5-furylpyrazole

Title compound was obtained by using the manufacturing method same as in the above Example 7.

Yield: 57.6%

$^1$H NMR (300 MHz, CDCl$_3$) δ 7.40-7.49 (m, 6H), 7.20 (br, 1H), 6.63 (s, 1H), 6.33-6.34 (m, 1H), 5.98 (d, J=3.40 Hz, 1H), 4.60 (d, J=5.49 Hz, 2H), 4.12 (s, 2H)

Example 10

Synthesis of 1-chloroacetyl-4-phenylpiperazine

Phenylpiperazine (2.434 g, 15 mmol) was dissolved in 20 mL of purified methylene chloride, dropwisely added with chloroacetyl chloride (1.194 mL, 15 mmol) at 0° C. and then stirred at room temperature. Completion of the reaction was confirmed by TLC (hexane:ethyl acetate=1:1). Upon completion of reaction, the reaction mixture was adjusted to pH 7 using saturated NaHCO$_3$ and extracted with methylene chloride. The resulting organic layer was dried with anhydrous magnesium sulfate and filtered, and the filtrate was concentrated and dried in vacuo to obtain the title compound.

Yield: 97.0%

$^1$H NMR (300 MHz, CDCl$_3$) δ 7.26-7.32 (m, 2H), 6.90-6.96 (m, 3H), 4.12 (s, 2H), 3.79 (t, J=5.00 Hz, 2H), 3.68 (t, J=4.84 Hz, 2H), 3.24 (t, J=5.21 Hz, 3.18 (t, J=5.25 Hz, 2H)

Example 11

Synthesis of 1-chloroacetyl-4-(2,3-dimethylphenyl)piperazine

Title compound was obtained by using the manufacturing method same as in the above Example 10.

Yield: 86.7%

$^1$H NMR (300 MHz, CDCl$_3$) δ 7.10 (t, J=7.63 Hz, 1H), 6.96 (d, J=7.11 Hz, 1H), 3.88 (d, J=7.76 Hz, 2H), 4.14 (s, 2H), 3.97 (br, 2H), 3.65 (br, 2H), 2.92 (br, 2H), 2.85 (br, 2H), 2.30 (s, 3H), 2.28 (s, 3H)

Example 12

Synthesis of 1-chloroacetyl-4-(2,4-dimethylphenyl)piperazine

Title compound was obtained by using the manufacturing method same as in the above Example 10.

Yield: 95.37%

$^1$H NMR (300 MHz, CDCl$_3$) δ 6.99-7.04 (m, 2H), 6.89-6.92 (m, 1H), 4.14 (s, 2H), 3.79 (t, J=6.09 Hz, 2H), 3.66 (t, J=4.53 Hz, 2H), 2.94 (t, J=4.82 Hz, 2H), 2.88 (t, J=4.79 Hz, 2H), 2.31 (s, 3H), 2.30 (s, 3H)

Example 13

Synthesis of 1-chloroacetyl-4-benzhydrylpiperazine

Title compound was obtained by using the manufacturing method same as in the above Example 10.

Yield: 97.4%

$^1$H NMR (300 MHz, CDCl$_3$) δ 7.44 (d, J=7.38 Hz, 4H), 7.30 (t, J=7.18 Hz, 4H), 7.21 (t, J=7.20 Hz, 2H), 4.27 (s, 1H), 4.03 (s, 2H), 3.64 (t, J=4.98 Hz, 2H), 3.50 (t, J=4.75 Hz, 2H), 2.40-2.46 (m, 4H)

Example 14

Synthesis of 1-chloroacetyl-4-(3,4-dichlorobenzyl)piperazine

Title compound was obtained by using the manufacturing method same as in the above Example 10.

Yield: 95.4%

$^1$H NMR (300 MHz, CDCl$_3$) δ 7.44 (s, 1H), 7.37 (s, 1H), 7.16 (d, J=6.42 Hz, 1H), 4.06 (s, 2H), 3.63 (t, J=5.04 Hz, 2H), 3.52 (t, J=4.89 Hz, 2H), 2.42-2.49 (m, 4H)

Example 15

Synthesis of 3-{[4-(2,3-dimethyl)phenylpiperazin-1-yl]methylcarboxamido}methyl-5-methyl-1-phenyl-1H-pyrazole (Compound No. 1)

4-(2,3-Dimethylphenyl)piperazine (0.095 g, 0.5 mmol) and K$_2$CO$_3$ (0.138 g, 1 mmol) were dissolved in 7 mL of purified acetonitrile and then stirred at 50° C. for about 30 minutes. Then, the reaction mixture was dropwisely added with 3-(2-chloroacetimido)methyl-1-phenyl-5-methylpyrazole (0.132 g, 0.5 mmol), which was prepared in Example 7, and stirred at 80° C. Completion of the reaction was confirmed by TLC (ethyl acetate). Upon completion of reaction, water was added to the reaction mixture and the resulting mixture was extracted with methylene chloride. The resulting organic layer was dried with anhydrous magnesium sulfate and filtered, and the filtrate was concentrated under reduced pressure and purified by column chromatography (ethyl acetate) to obtain the title compound.

Yield: 46.9%

$^1$H NMR (300 MHz, CDCl$_3$) δ 7.83 (br, 1H), 7.44-7.47 (m, 4H), 7.38-7.41 (m, 1H), 7.07 (t, J=7.69 Hz, 1H), 6.92 (d, J=7.27 Hz, 1H), 6.86 (d, J=7.86 Hz, 1H), 6.16 (s, 1H), 4.55 (d, J=5.63 Hz, 2H), 3.15 (s, 1H), 2.89-2.92 (m, 4H), 2.73 (br, 4H), 2.34 (s, 3H), 2.28 (s, 3H), 2.06 (s, 3H)

Example 16

Synthesis of 3-[(4-phenylpiperazin-1-yl)methylcarboxamido]methyl-5-methyl-1-phenyl-1H-pyrazole (Compound No. 2)

Title compound was obtained by using the manufacturing method same as in the above Example 15.

Yield: 40.0%

$^1$H NMR (300 MHz, CDCl$_3$) δ 7.73 (br, 1H), 7.37-7.45 (m, 5H), 7.27 (t, J=8.13 Hz, 2H), 6.88 (d, J=8.00 Hz, 3H), 6.16 (s, 1H), 4.53 (d, J=5.60 Hz, 2H), 3.19 (t, J=4.63 Hz, 4H), 3.14 (s, 2H), 2.72 (t, J=5.06 Hz, 4H), 2.33 (s, 3H)

Example 17

Synthesis of 3-[(4-benzhydrylpiperazin-1-yl)methylcarboxamido]methyl-5-methyl-1-phenyl-1H-pyrazole (Compound No. 3)

Title compound was obtained by using the manufacturing method same as in the above Example 15.

Yield: 66.3%

$^1$H NMR (300 MHz, CDCl$_3$) δ 7.70 (br, 1H), 7.38-7.44 (m, 8H), 7.27-7.30 (m, 5H), 7.16-7.19 (m, 2H), 6.11 (s, 1H), 4.48 (d, J=5.82 Hz, 2H), 4.18 (s, 1H), 3.06 (s, 2H), 2.57 (br, 4H), 2.40 (br, 4H), 2.31 (s, 3H)

Example 18

Synthesis of 3-{[4-(2,4-dimethylphenyl)piperazin-1-yl]methylcarboxamido}methyl-5-methyl-1-phenyl-1H-pyrazole (Compound No. 4)

Title compound was obtained by using the manufacturing method same as in the above Example 15.

Yield: 25.6%

$^1$H NMR (300 MHz, CDCl$_3$) δ 7.83 (br, 1H), 7.39-7.48 (m, 5H), 6.96-7.01 (m, 2H), 6.85-6.88 (m, 1H), 6.17 (s, 1H), 4.54 (d, J=5.62 Hz, 2H), 3.14 (s, 2H), 2.88-2.93 (m, 6H), 2.71 (br, 4H), 2.34 (s, 3H), 2.29 (s, 3H), 2.26 (s, 3H)

Example 19

Synthesis of 3-{[4-(3-trifluoromethyl)benzylpiperazin-1-yl]methylcarboxamido}methyl-5-methyl-1-phenyl-1H-pyrazole (Compound No. 5)

Title compound was obtained by using the manufacturing method same as in the above Example 15.

Yield: 35.5%

$^1$H NMR (300 MHz, CDCl$_3$) δ 7.71 (br, 1H), 7.38-7.55 (m, 9H), 6.13 (s, 1H), 4.50 (d, J=5.60 Hz, 2H), 3.52 (s, 2H), 3.07 (s, 2H), 2.58 (br, 4H), 2.46 (br, 4H), 2.32 (s, 3H)

Example 20

Synthesis of 3-{[4-(3,4-dichlorobenzyl)piperazin-1-yl]methylcarboxamido}methyl-5-methyl-1-phenyl-1H-pyrazole (Compound No. 6)

Title compound was obtained by using the manufacturing method same as in the above Example 15.

Yield: 49.3%

$^1$H NMR (300 MHz, CDCl$_3$) δ 7.69 (br, 1H), 7.36-7.48 (m, 7H), 7.15-7.17 (m, 1H), 6.13 (s, 1H), 4.50 (d, J=5.73 Hz, 2H), 3.41 (s, 2H), 3.06 (s, 2H), 2.57 (br, 4H), 2.44 (br, 4H), 2.32 (s, 3H)

Example 21

Synthesis of 3-{[4-(4-trifluoromethyl)benzylpiperazin-1-yl]methylcarboxamido}methyl-5-methyl-1-phenyl-1H-pyrazole (Compound No. 7)

Title compound was obtained by using the manufacturing method same as in the above Example 15.
Yield: 28.7%
$^1$H NMR (300 MHz, CDCl$_3$) δ 7.69 (br, 1H), 7.55-7.58 (m, 2H), 7.27-7.50 (m, 7H), 6.14 (s, 1H), 4.50 (d, J=5.75 Hz, 2H), 3.52 (s, 2H), 3.06 (s, 2H), 2.57 (br, 4H), 2.46 (br, 4H), 2.32 (s, 3H)

Example 22

Synthesis of 3-{[4-(2,3,4-trimethoxy)benzylpiperazin-1-yl]methylcarboxamido}methyl-5-methyl-1-phenyl-1H-pyrazole (Compound No. 8)

Title compound was obtained by using the manufacturing method same as in the above Example 15.
Yield: 32.4%
$^1$H NMR (300 MHz, CDCl$_3$) δ 7.47 (br, 1H), 7.37-7.45 (m, 5H), 6.95 (d, J=8.52 Hz, 1H), 6.63 (d, J=8.55 Hz, 1H), 6.13 (s, 1H), 4.49 (d, J=5.76 Hz, 2H), 3.86 (s, 6H), 3.84 (s, 3H), 3.45 (s, 2H), 3.04 (s, 2H), 2.55 (br, 4H), 2.48 (br, 4H), 2.32 (s, 3H)

Example 23

Synthesis of 3-[(4-phenylpiperazin-1-yl)methylcarboxamido]methyl-5-isobutyl-1-phenyl-1H-pyrazole (Compound No. 9)

Title compound was obtained by using the manufacturing method same as in the above Example 15.
Yield: 62.8%
$^1$H NMR (300 MHz, CDCl$_3$) δ 7.73 (br, 1H), 7.36-7.46 (m, 5H), 7.26 (t, J=6.24 Hz, 2H), 6.88 (d, J=6.99 Hz, 3H), 6.15 (s, 1H), 4.55 (d, J=5.60 Hz, 2H), 3.13-3.22 (m, 6H), 2.69-2.72 (m, 4H), 2.51 (d, J=7.17 Hz, 2H), 1.80-1.84 (m, 1H), 0.90 (s, 3H), 0.85 (s, 3H)

Example 24

Synthesis of 3-{[4-(2,3-dimethylphenyl)piperazin-1-yl]methylcarboxamido}methyl-5-isobutyl-1-phenyl-1H-pyrazole (Compound No. 10)

Title compound was obtained by using the manufacturing method same as in the above Example 15.
Yield: 63.0%
$^1$H NMR (300 MHz, CDCl$_3$) δ 7.82 (br, 1H), 7.39-7.49 (m, 5H), 7.07 (t, J=7.61 Hz, 1H), 6.92 (d, J=7.34 Hz, 1H), 6.83 (d, J=7.89 Hz, 1H), 6.16 (s, 1H), 4.56 (d, J=5.60 Hz, 2H), 3.15 (s, 2H), 2.87-2.90 (m, 4H), 2.72 (br, 4H), 2.52 (d, J=7.16 Hz, 2H), 2.27 (s, 3H), 2.21 (s, 3H), 1.81-1.85 (m, 1H), 0.88 (s, 3H), 0.86 (s, 3H)

Example 25

Synthesis of 3-[(4-phenylpiperazin-1-yl)methylcarboxamido]methyl-5-furyl-1-phenyl-1H-pyrazole (Compound No. 11)

Title compound was obtained by using the manufacturing method same as in the above Example 15.
Yield: 73.5%
$^1$H NMR (300 MHz, CDCl$_3$) δ 7.77 (br, 1H), 7.39-7.44 (m, 6H), 7.27 (t, J=6.94 Hz, 2H), 6.85-6.90 (m, 3H), 6.62 (s, 1H), 6.32-6.34 (m, 1H), 5.99 (d, J=3.32 Hz, 1H), 4.60 (d, J=5.68 Hz, 2H), 3.15-3.20 (m, 6H), 2.72 (t, J=5.09 Hz, 4H)

Example 26

Synthesis of 3-{[4-(2,3-dimethylphenyl)piperazin-1-yl]methylcarboxamido}methyl-5-furyl-1-phenyl-1H-pyrazole (Compound No. 12)

Title compound was obtained by using the manufacturing method same as in the above Example 15.
Yield: 82.3%
$^1$H NMR (300 MHz, CDCl$_3$) δ 7.86 (br, 1H), 7.39-7.44 (m, 6H), 7.08 (t, J=7.69 Hz, 1H), 6.92 (d, J=7.30 Hz, 1H), 6.85 (d, J=7.91 Hz, 1H), 6.63 (s, 1H), 6.33-6.35 (m, 1H), 6.00 (d, J=3.40 Hz, 1H), 4.61 (d, J=5.71 Hz, 2H), 3.17 (s, 2H), 2.90 (t, J=4.48 Hz, 4H), 2.75 (br, 4H), 2.28 (s, 3H), 2.22 (s, 3H)

Example 27

Synthesis of 3-{[4-(3-trifluoromethylbenzyl)piperazin-1-yl]methylcarboxamido}methyl-5-furyl-1-phenyl-1H-pyrazole (Compound No. 13)

Title compound was obtained by using the manufacturing method same as in the above Example 15.
Yield: 68.0%
$^1$H NMR (300 MHz, CDCl$_3$) δ 7.73 (br, 1H), 7.37-7.55 (m, 10H), 6.59 (s, 1H), 6.33 (s, 1H), 5.98 (d, J=3.38 Hz, 1H), 4.57 (d, J=5.77 Hz, 2H), 3.51 (s, 2H), 3.08 (s, 2H), 2.58 (br, 4H), 2.45 (br, 4H)

Example 28

Synthesis of 3-{[4-(4-trifluoromethylbenzyl)piperazin-1-yl]methylcarboxamido}methyl-5-furyl-1-phenyl-1H-pyrazole (Compound No. 14)

Title compound was obtained by using the manufacturing method same as in the above Example 15.
Yield: 80.9%
$^1$H NMR (300 MHz, CDCl$_3$) δ 7.72 (br, 1H), 7.56 (d, J=8.00 Hz, 2H), 7.38-7.45 (m, 8H), 6.60 (s, 1H), 6.32-6.33 (m, 1H), 5.99 (d, J=3.25 Hz, 1H), 4.57 (d, J=5.78 Hz, 2H), 3.52 (s, 2H), 3.08 (s, 2H), 2.58 (br, 4H), 2.45 (br, 4H)

Example 29

Synthesis of 3-{[4-(2,3-dimethylphenyl)piperazin-1-yl]carbonylmethylamino}methyl-5-methyl-1H-pyrazole (Compound No. 95)

Yield: 42.5%
$^1$H NMR (300 MHz, CDCl$_3$) δ 7.08 (t, J=7.67 Hz, 1H), 6.94 (d, J=7.45 Hz, 1H), 6.85 (d, J=7.73 Hz, 1H), 6.00 (s, 1H), 3.93 (s, 2H), 3.49-3.76 (m, 4H), 2.84-2.85 (m, 4H), 2.33 (s, 3H), 2.28 (s, 3H), 2.23 (s, 3H)

Example 30

Synthesis of 3-{[4-(3-trifluoromethylbenzyl)piperazin-1-yl]methylcarboxamido}methyl-5-isobutyl-1-phenyl-1H-pyrazole (Compound No. 15)

Title compound was obtained by using the manufacturing method same as in the above Example 15.

Yield: 61.0%

$^1$H NMR (300 MHz, CDCl$_3$) δ 7.69 (br, 1H), 7.36-7.54 (m, 9H), 6.12 (s, 1H), 4.51 (d, J=5.71 Hz, 2H), 3.49 (s, 2H), 3.05 (s, 2H), 2.56 (br, 4H), 2.49 (d, J=7.17 Hz, 2H), 2.43 (br, 4H), 1.77-1.82 (m, 1H), 0.85 (s, 3H), 0.83 (s, 3H)

Example 31

Synthesis of 3-{[4-(4-trifluoromethylbenzyl)piperazin-1-yl]methylcarboxamido}methyl-5-isobutyl-1-phenyl-1H-pyrazole (Compound No. 16)

Title compound was obtained by using the manufacturing method same as in the above Example 15.

Yield: 53.9%

$^1$H NMR (300 MHz, CDCl$_3$) δ 7.68 (br, 1H), 7.55 (d, J=7.68 Hz, 2H), 7.45-7.39 (m, 7H), 6.12 (s, 1H), 4.51 (d, J=5.38 Hz, 2H), 3.51 (s, 2H), 3.06 (s, 2H), 2.56 (br, 4H), 2.50 (d, J=7.08 Hz, 2H), 2.43 (br, 4H), 1.85 (m, 1H), 0.86 (s, 3H), 0.84 (s, 3H)

Example 32

Synthesis of 3-{[4-(2,3,4-trimethoxy)benzylpiperazin-1-yl]methylcarboxamido}methyl-5-isobutyl-1-phenyl-1H-pyrazole (Compound No. 17)

Title compound was obtained by using the manufacturing method same as in the above Example 15.

Yield: 50.8%

$^1$H NMR (300 MHz, CDCl$_3$) δ 7.70 (t, J=5.46 Hz, 1H), 7.27-7.50 (m, 5H), 6.94 (d, J=8.49 Hz, 1H), 6.63 (d, J=8.52 Hz, 1H), 6.12 (s, 1H), 4.50 (d, J=5.28 Hz, 2H), 3.82-3.86 (m, 9H), 3.43 (s, 2H), 3.03 (s, 2H), 2.47-2.54 (m, 10H), 1.79-1.83 (m, 1H), 0.84 (d, J=6.57 Hz, 6H)

Example 33

Synthesis of 3-{[4-(2,3,4-trimethoxy)benzylpiperazin-1-yl]methylcarboxamido}methyl-5-furyl-1-phenyl-1H-pyrazole (Compound No. 18)

Title compound was obtained by using the manufacturing method same as in the above Example 15.

Yield: 51.3%

$^1$H NMR (300 MHz, CDCl$_3$) δ 7.74 (br, 1H), 7.38-7.44 (m, 6H), 6.96 (d, J=8.52 Hz, 2H), 3.85 (d, J=5.41 Hz, 9H), 3.45 (s, 2H), 3.06 (s, 2H), 2.48-2.56 (br, 8H)

Example 34

Synthesis of 3-[(4-benzhydrylpiperazin-1-yl)methylcarboxamido]methyl-5-isobutyl-1-phenyl-1H-pyrazole (Compound No. 19)

Title compound was obtained by using the manufacturing method same as in the above Example 15.

Yield: 45.0%

$^1$H NMR (300 MHz, CDCl$_3$) δ 7.69 (br, 1H), 7.36-7.46 (m, 9H), 7.15-7.30 (m, 6H), 6.12 (s, 1H), 4.52 (d, J=5.75 Hz, 2H), 4.18 (s, 1H), 3.07 (s, 2H), 2.57 (br, 4H), 2.49 (d, J=7.19 Hz, 2H), 2.40 (br, 4H), 1.77-1.82 (m, 1H), 0.87 (d, J=11.3 Hz, 6H)

Example 35

Synthesis of 3-[(4-benzhydrylpiperazin-1-yl)methylcarboxamido]methyl-5-furyl-1-phenyl-1H-pyrazole (Compound No. 20)

Title compound was obtained by using the manufacturing method same as in the above Example 15.

Yield: 47.2%

$^1$H NMR (300 MHz, CDCl$_3$) δ 7.75 (br, 1H), 7.37-7.42 (m, 9H), 7.25-7.30 (m, 4H), 7.16-7.21 (m, 2H), 6.60 (s, 1H), 6.32 (s, 1H), 5.99 (d, J=3.19 Hz, 1H), 4.57 (d, J=5.79 Hz, 2H), 4.20 (s, 1H), 3.09 (s, 2H), 2.59 (br, 4H), 2.42 (br, 4H)

Example 36

Synthesis of 3-[(4-piperonylpiperazin-1-yl)methylcarboxamido]methyl-5-isobutyl-1-phenyl-1H-pyrazole (Compound No. 21)

Title compound was obtained by using the manufacturing method same as in the above Example 15.

Yield: 55.2%

$^1$H NMR (300 MHz, CDCl$_3$) δ 7.69 (br, 1H), 7.38-7.49 (m, 5H), 4.51 (d, J=5.75 Hz, 2H), 3.36 (s, 2H), 3.05 (s, 2H), 2.55 (br, 4H), 2.50 (d, J=7.19 Hz, 2H), 2.41 (br, 4H), 1.76-1.85 (m, 1H), 0.85 (d, J=6.62 Hz, 6H)

Example 37

Synthesis of 3-[(4-piperonylpiperazin-1-yl)methylcarboxamido]methyl-5-furyl-1-phenyl-1H-pyrazole (Compound No. 22)

Title compound was obtained by using the manufacturing method same as in the above Example 15.

Yield: 53.0%

$^1$H NMR (300 MHz, CDCl$_3$) δ 7.74 (br, 1H), 7.38-7.45 (m, 6H), 6.81 (s, 1H), 6.71-6.73 (m, 2H), 6.59 (s, 1H), 6.32 (s, 1H), 5.99 (s, 1H), 5.93 (s, 2H), 4.55 (d, J=6.00 Hz, 2H), 3.38 (s, 2H), 3.06 (s, 2H), 2.56 (br, 4H), 2.43 (br, 4H)

Example 38

Synthesis of 3-{[4-(3,4-dichloro)benzylpiperazin-1-yl]methylcarboxamido}methyl-5-furyl-1-phenyl-1H-pyrazole (Compound No. 23)

Title compound was obtained by using the manufacturing method same as in the above Example 15.

Yield: 70.1%

$^1$H NMR (300 MHz, CDCl$_3$) δ 7.72 (br, 1H), 7.35-7.46 (m, 8H), 7.12 (d, J=6.45 Hz, 1H), 6.59 (s, 1H), 6.32 (d, J=1.80 Hz, 1H), 5.98 (d, J=3.42 Hz, 1H), 4.56 (d, J=5.79 Hz, 2H), 3.40 (s, 2H), 3.08 (s, 2H), 2.43-2.57 (m, 8H)

Example 39

Synthesis of 3-{[4-(3,4-dichloro)benzylpiperazin-1-yl]methylcarboxamido}methyl-5-isobutyl-1H-pyrazole (Compound No. 24)

Title compound was obtained by using the manufacturing method same as in the above Example 15.

Yield: 68.1%

$^1$H NMR (300 MHz, CDCl$_3$) δ 7.69 (br, 1H), 7.34-7.46 (m, 7H), 7.10 (d, J=1.83 Hz, 1H), 6.12 (s, 1H), 4.50 (d, J=5.73 Hz, 2H), 3.38 (s, 2H), 3.05 (s, 2H), 2.55 (br, 4H), 2.49 (d, J=7.17 Hz, 2H), 2.41 (br, 4H), 1.75-1.84 (m, 1H), 0.85 (s, 3H), 0.83 (s, 3H)

Example 40

Synthesis of 3-{[4-(4-chlorophenyl)(phenyl)methylpiperazin-1-yl]methylcarboxamido}methyl-5-methyl-1-phenyl-1H-pyrazole (Compound No. 25)

Title compound was obtained by using the manufacturing method same as in the above Example 15.

Yield: 62.3%

$^1$H NMR (300 MHz, CDCl$_3$) δ 7.70 (br, 1H), 7.18-7.41 (m, 14H), 6.12 (s, 1H), 4.49 (d, J=5.76 Hz, 2H), 4.16 (s, 1H), 3.06 (s, 2H), 2.51 (br, 4H), 2.39 (br, 4H), 2.30 (s, 3H)

Example 41

Synthesis of 3-{[4-(4-chlorophenyl)(phenyl)methylpiperazin-1-yl]methylcarboxamido}methyl-5-furyl-1-phenyl-1H-pyrazole (Compound No. 26)

Title compound was obtained by using the manufacturing method same as in the above Example 15.

Yield: 51.2%

$^1$H NMR (300 MHz, CDCl$_3$) δ 7.72 (br, 1H), 7.23-7.42 (m, 15H), 6.58 (s, 1H), 6.32 (s, 1H), 5.98 (d, J=3.40 Hz, 1H), 4.55 (d, J=5.84 Hz, 2H), 4.17 (s, 1H), 3.08 (s, 2H), 2.58 (br, 4H), 2.39 (br, 4H)

Example 42

Synthesis of 3-[(4-phenylpiperazin-1-yl)methylcarboxamido}methyl-5-propyl-1-phenyl-1H-pyrazole (Compound No. 27)

Title compound was obtained by using the manufacturing method same as in the above Example 15.

Yield: 52.8%

$^1$H NMR (300 MHz, CDCl$_3$) δ 7.74 (br, 1H), 7.38-7.45 (m, 5H), 7.27 (t, J=7.61 Hz, 2H), 6.85-6.90 (m, 3H), 6.17 (s, 1H), 4.54 (d, J=5.63 Hz, 2H), 3.18 (t, J=4.73 Hz, 4H), 3.14 (s, 2H), 2.71 (t, J=4.88 Hz, 4H), 2.61 (t, J=7.57 Hz, 2H), 1.58-1.65 (m, 2H), 0.92 (t, J=7.33 Hz, 3H)

Example 43

Synthesis of 3-{[4-(2,3-dimethyl)phenylpiperazin-1-yl]methylcarboxamido}methyl-5-propyl-1-phenyl-1H-pyrazole (Compound No. 28)

Title compound was obtained by using the manufacturing method same as in the above Example 15.

Yield: 49.8%

$^1$H NMR (300 MHz, CDCl$_3$) δ 7.83 (br, 1H), 7.40-7.48 (m, 5H), 7.08 (t, J=7.69 Hz, 1H), 6.92 (d, J=7.33 Hz, 1H), 6.84 (d, J=7.83 Hz, 1H), 6.19 (s, 1H), 4.55 (d, J=5.64 Hz, 2H), 3.16 (s, 2H), 2.89 (t, J=4.49 Hz, 4H), 2.73 (br, 4H), 2.62 (t, J=7.57 Hz, 2H), 2.27 (s, 3H), 2.21 (s, 3H), 1.56-1.66 (m, 2H), 0.93 (t, J=7.2 Hz, 3H)

Example 44

Synthesis of 3-{[4-(2,4-dimethyl)phenylpiperazin-1-yl]methylcarboxamido}methyl-5-propyl-1-phenyl-1H-pyrazole (Compound No. 29)

Title compound was obtained by using the manufacturing method same as in the above Example 15.

Yield: 46.6%

$^1$H NMR (300 MHz, CDCl$_3$) δ 7.84 (br, 1H), 7.38-7.50 (m, 5H), 6.96-7.01 (m, 2H), 6.86 (d, J=7.93 Hz, 1H), 6.18 (s, 1H), 4.55 (d, J=5.64 Hz, 2H), 3.14 (s, 2H), 2.87-2.90 (m, 4H), 2.71 (br, 4H), 2.62 (t, J=7.56 Hz, 2H), 2.29 (s, 3H), 2.26 (s, 3H), 1.56-1.66 (m, 2H), 0.93 (t, J=7.32 Hz, 3H)

Example 45

Synthesis of 3-[(4-benzhydrylpiperazin-1-yl)methylcarboxamido]methyl-5-propyl-1-phenyl-1H-pyrazole (Compound No. 30)

Title compound was obtained by using the manufacturing method same as in the above Example 15.

Yield: 55.9%

$^1$H NMR (300 MHz, CDCl$_3$) δ 7.70 (br, 1H), 7.38-7.44 (m, 9H), 7.18-7.30 (m, 6H), 6.13 (s, 1H), 4.50 (d, J=5.81 Hz, 2H), 4.18 (s, 1H), 3.07 (s, 2H), 2.40-2.61 (m, 10H), 1.55-1.63 (m, 2H), 0.91 (t, J=7.28 Hz, 3H)

Example 46

Synthesis of 3-{[4-(3-trifluoromethyl)benzylpiperazin-1-yl]methylcarboxamido}methyl-5-propyl-1-phenyl-1H-pyrazole (Compound No. 31)

Title compound was obtained by using the manufacturing method same as in the above Example 15.

Yield: 53.7%

$^1$H NMR (300 MHz, CDCl$_3$) δ 7.71 (br, 1H), 7.38-7.53 (m, 9H), 6.15 (s, 1H), 4.51 (d, J=5.70 Hz, 2H), 3.48 (s, 2H), 3.07 (s, 2H), 2.45-2.62 (m, 10H), 1.57-1.64 (m, 2H), 0.92 (t, J=5.67 Hz, 3H)

Example 47

Synthesis of 3-{[4-(4-trifluoromethyl)benzylpiperazin-1-yl]methylcarboxamido}methyl-5-propyl-1-phenyl-1H-pyrazole (Compound No. 32)

Title compound was obtained by using the manufacturing method same as in the above Example 15.

Yield: 43.3%

$^1$H NMR (300 MHz, CDCl$_3$) δ 7.70 (br, 1H), 7.56 (d, J=8.01 Hz, 2H), 7.37-7.50 (m, 7H), 6.15 (s, 1H), 4.51 (d, J=5.72 Hz, 2H), 3.52 (s, 2H), 3.06 (s, 2H), 2.45-2.62 (m, 10H), 1.56-1.64 (m, 2H), 0.91 (t, J=7.34 Hz, 3H)

Example 48

Synthesis of 3-[(4-piperonylpiperazin-1-yl)methylcarboxamido]methyl-5-propyl-1-phenyl-1H-pyrazole (Compound No. 33)

Title compound was obtained by using the manufacturing method same as in the above Example 15.

Yield: 51.1%

$^1$H NMR (300 MHz, CDCl$_3$) δ 7.70 (br, 1H), 7.37-7.50 (m, 5H), 6.81 (s, 1H), 6.70-6.75 (m, 2H), 5.93 (s, 1H), 5.91 (s, 2H), 4.50 (d, J=5.76 Hz, 2H), 3.35 (s, 2H), 3.05 (s, 2H), 2.42-2.62 (m, 10H), 1.56-1.64 (m, 2H), 0.91 (t, J=7.29 Hz, 3H)

Example 49

Synthesis of 3-{[4-(2-pyridyl)piperazin-1-yl]methylcarboxamido}methyl-5-methyl-1-phenyl-1H-pyrazole (Compound No. 34)

Title compound was obtained by using the manufacturing method same as in the above Example 15.

Yield: 53.0%

$^1$H NMR (300 MHz, CDCl$_3$) δ 8.18 (d, J=3.80 Hz, 1H), 7.71 (br, 1H), 7.35-7.50 (m, 6H), 6.59-6.65 (m, 2H), 6.15 (s, 1H), 4.53 (d, J=5.65 Hz, 2H), 3.53 (t, J=4.87 Hz, 4H), 3.12 (s, 2H), 2.65 (t, J=5.00 Hz, 4H), 2.32 (s, 3H)

Example 50

Synthesis of 3-{[4-(2-pyrimidyl)piperazin-1-yl]methylcarboxamido}methyl-5-methyl-1-phenyl-1H-pyrazole (Compound No. 35)

Title compound was obtained by using the manufacturing method same as in the above Example 15.

Yield: 47.0%

$^1$H NMR (300 MHz, CDCl$_3$) δ 8.28 (d, J=4.74 Hz, 2H), 7.70 (br, 1H), 7.32-7.47 (m, 5H), 6.47 (t, J=4.74 Hz, 1H), 6.14 (s, 1H), 4.51 (d, J=5.70 Hz, 2H), 3.81 (t, J=4.83 Hz, 4H), 3.09 (s, 2H)

Example 51

Synthesis of 3-{[4-(2-pyridyl)piperazin-1-yl]methylcarboxamido}methyl-5-isobutyl-1-phenyl-1H-pyrazole (Compound No. 36)

Title compound was obtained by using the manufacturing method same as in the above Example 15.

Yield: 65.8%

$^1$H NMR (300 MHz, CDCl$_3$) δ 8.15 (d, J=3.09 Hz, 1H), 7.86 (br, 1H), 7.34-7.45 (m, 6H), 6.56-6.61 (m, 2H), 6.13 (s, 1H), 4.52 (d, J=5.64 Hz, 2H), 3.50 (t, J=4.62 Hz, 4H), 3.09 (s, 2H), 2.62 (t, J=4.80 Hz, 4H), 2.48 (d, J=7.17 Hz, 2H), 1.75-1.84 (m, 1H), 0.85 (s, 3H), 0.82 (s, 3H)

Example 52

Synthesis of 3-{[4-(2-pyrimidyl)piperazin-1-yl]methylcarboxamido}methyl-5-isobutyl-1-phenyl-1H-pyrazole (Compound No. 37)

Title compound was obtained by using the manufacturing method same as in the above Example 15.

Yield: 65.8%

$^1$H NMR (300 MHz, CDCl$_3$) δ 8.27 (d, J=4.77 Hz, 2H), 7.70 (br, 1H), 7.34-7.47 (m, 5H), 6.47 (t, J=4.71 Hz, 1H), 6.14 (s, 1H), 4.53 (d, J=5.70 Hz, 2H), 3.79 (t, J=4.74 Hz, 4H), 3.08 (s, 2H), 2.57 (t, J=4.83 Hz, 4H), 2.48 (d, J=7.17 Hz, 2H), 1.75-1.84 (m, 1H), 0.85 (s, 3H), 0.83 (s, 3H)

Example 53

Synthesis of 3-{[4-(2-pyridyl)piperazin-1-yl]methylcarboxamido}methyl-5-furyl-1-phenyl-1H-pyrazole (Compound No. 38)

Title compound was obtained by using the manufacturing method same as in the above Example 15.

Yield: 45.2%

$^1$H NMR (300 MHz, CDCl$_3$) δ 8.18 (d, J=3.66 Hz, 1H), 7.85 (br, 1H), 7.38-7.47 (m, 7H), 6.59-6.63 (m, 3H), 6.32-6.34 (m, 1H), 5.97 (d, J=3.39 Hz, 1H), 4.60 (d, J=5.73 Hz, 2H), 3.53 (t, J=4.83 Hz, 4H), 3.14 (s, 2H), 2.66 (t, J=5.04 Hz, 4H)

Example 54

Synthesis of 3-{[4-(2-pyrimidyl)piperazin-1-yl]methylcarboxamido}methyl-5-furyl-1-phenyl-1H-pyrazole (Compound No. 39)

Title compound was obtained by using the manufacturing method same as in the above Example 15.

Yield: 56.5%

$^1$H NMR (300 MHz, CDCl$_3$) δ 8.29 (d, J=2.34 Hz, 2H), 7.80 (br, 1H), 7.38-7.45 (m, 6H), 6.61 (s, 1H), 6.48 (t, J=4.74 Hz, 1H), 6.31-6.33 (m, 1H), 5.96 (d, J=3.36 Hz, 1H), 4.59 (d, J=5.73 Hz, 2H), 3.82 (t, J=4.89 Hz, 4H), 3.12 (s, 2H), 2.60 (t, J=5.04 Hz, 4H)

Example 55

Synthesis of 3-{[4-(4-t-butyl)benzylpiperazin-1-yl]methylcarboxamido}methyl-5-methyl-1-phenyl-1H-pyrazole (Compound No. 40)

Title compound was obtained by using the manufacturing method same as in the above Example 15.

Yield: 58.7%

$^1$H NMR (300 MHz, CDCl$_3$) δ 7.47 (br, 1H), 7.41-7.45 (m, 5H), 7.35 (d, J=9.71 Hz, 2H), 7.21 (d, J=8.24 Hz, 2H), 6.14 (s, 1H), 4.50 (d, J=5.75 Hz, 2H), 3.45 (s, 2H), 3.06 (s, 2H), 2.46-2.57 (br, 8H), 2.32 (s, 3H), 1.32 (s, 9H)

Example 56

Synthesis of 3-{[4-(2,4,6-trimethyl)benzylpiperazin-1-yl]methylcarboxamido}methyl-5-methyl-1-phenyl-1H-pyrazole (Compound No. 41)

Title compound was obtained by using the manufacturing method same as in the above Example 15.

Yield: 66.3%

$^1$H NMR (300 MHz, CDCl$_3$) δ 7.80 (br, 1H), 7.40-7.51 (m, 5H), 6.83 (s, 2H), 6.16 (s, 1H), 4.52 (d, J=5.65 Hz, 2H), 3.44 (s, 2H), 3.04 (s, 2H), 2.47 (br, 8H), 2.34 (s, 9H), 2.27 (s, 3H)

Example 57

Synthesis of 3-{[4-(4-t-butyl)benzylpiperazin-1-yl]methylcarboxamido}methyl-5-isobutyl-1-phenyl-1H-pyrazole (Compound No. 42)

Title compound was obtained by using the manufacturing method same as in the above Example 15.

Yield: 56.7%

$^1$H NMR (300 MHz, CDCl$_3$) δ 7.72 (br, 1H), 7.37-7.46 (m, 5H), 7.32 (d, J=8.14 Hz, 2H), 7.20 (d, J=7.98 Hz, 2H), 6.13 (s, 1H), 4.52 (d, J=5.68 Hz, 2H), 3.44 (s, 2H), 3.05 (s, 2H), 2.56 (br, 4H), 2.50 (d, J=7.20 Hz, 2H), 2.44 (br, 4H), 1.81-1.89 (m, 1H), 1.31 (s, 9H), 0.86 (s, 3H), 0.84 (s, 3H)

Example 58

Synthesis of 3-{[4-(2,4,6-trimethyl)benzylpiperazin-1-yl]methylcarboxamido}methyl-5-isobutyl-1-phenyl-1H-pyrazole (Compound No. 43)

Title compound was obtained by using the manufacturing method same as in the above Example 15.

Yield: 51.8%

$^1$H NMR (300 MHz, CDCl$_3$) δ 7.78 (br, 1H), 7.38-7.51 (m, 5H), 6.83 (s, 2H), 6.15 (s, 1H), 4.54 (d, J=5.70 Hz, 2H), 3.42 (s, 2H), 3.04 (s, 2H), 2.46-2.53 (m, 10H), 2.32 (s, 6H), 2.26 (s, 3H), 1.81-1.85 (m, 1H), 0.88 (s, 3H), 0.86 (s, 3H)

Example 59

Synthesis of 3-{[4-(2,3-dimethylphenyl)piperazin-1-yl]methylcarboxamido}methyl-5-(4-methoxy)phenyl-1-phenyl-1H-pyrazole (Compound No. 44)

Title compound was obtained by using the manufacturing method same as in the above Example 15.

Yield: 68.2%

$^1$H NMR (300 MHz, CDCl$_3$) δ 7.92 (br, 1H), 7.29-7.34 (m, 5H), 7.08-7.17 (m, 3H), 6.82-6.94 (m, 4H), 6.41 (s, 1H), 4.62 (d, J=5.66 Hz, 2H), 3.81 (s, 3H), 3.09 (s, 2H), 2.91 (t, J=4.51 Hz, 4H), 2.75 (br, 4H), 2.28 (s, 3H), 2.06 (s, 3H)

Example 60

Synthesis of 3-{[4-(2,4-dimethylphenyl)piperazin-1-yl]methylcarboxamido}methyl-5-(4-methoxy)phenyl-1-phenyl-1H-pyrazole (Compound No. 45)

Title compound was obtained by using the manufacturing method same as in the above Example 15.

Yield: 69.9%

$^1$H NMR (300 MHz, CDCl$_3$) δ 7.92 (br, 1H), 7.30-7.36 (m, 5H), 7.15 (d, J=8.78 Hz, 2H), 6.99 (t, J=8.26 Hz, 2H), 6.85 (q, J=5.15 Hz, 3H), 6.42 (s, 1H), 4.62 (d, J=5.64 Hz, 2H), 3.81 (s, 3H), 3.17 (s, 2H), 2.91 (t, J=4.16 Hz, 4H), 2.74 (br, 4H), 2.29 (s, 3H), 2.27 (s, 3H)

Example 61

Synthesis of 3-[(4-(4-furoylpiperazin-1-yl)methylcarboxamido]methyl-5-methyl-1-phenyl-1H-pyrazole (Compound No. 46)

Title compound was obtained by using the manufacturing method same as in the above Example 15.

Yield: 54.0%

$^1$H NMR (300 MHz, CDCl$_3$) δ 7.64 (br, 1H), 7.34-7.46 (m, 6H), 6.95 (d, J=3.39 Hz, 1H), 6.44 (d, J=3.36 Hz, 1H), 6.11 (s, 1H), 4.49 (d, J=5.61 Hz, 2H), 3.76 (br, 4H), 3.07 (s, 2H), 2.57 (t, J=4.95 Hz, 4H), 2.01 (s, 3H)

Example 62

Synthesis of 3-[(4-furoylpiperazin-1-yl)methylcarboxamido]methyl-5-isobutyl-1-phenyl-1H-pyrazole (Compound No. 47)

Title compound was obtained by using the manufacturing method same as in the above Example 15.

Yield: 66.1%

$^1$H NMR (300 MHz, CDCl$_3$) δ 7.63 (br, 1H), 7.31-7.44 (m, 6H), 6.93 (d, J=3.39 Hz, 1H), 6.43 (d, J=3.45 Hz, 1H), 6.10 (s, 1H), 4.50 (d, J=5.64 Hz, 2H), 3.68 (br, 4H), 3.06 (s, 2H), 2.56 (t, J=4.86 Hz, 4H), 2.46 (d, J=7.17 Hz, 2H), 1.72-1.81 (m, 1H), 0.82 (s, 3H), 0.80 (s, 3H)

Example 63

Synthesis of 3-{[4-(2-cyanophenyl)piperazin-1-yl]methylcarboxamido}methyl-5-methyl-1-phenyl-1H-pyrazole (Compound No. 48)

Title compound was obtained by using the manufacturing method same as in the above Example 15.

Yield: 75.9%

$^1$H NMR (300 MHz, CDCl$_3$) δ 7.72 (br, 1H), 7.52 (d, J=6.22 Hz, 1H), 7.38-7.45 (m, 6H), 6.99 (t, J=7.54 Hz, 1H), 6.90 (d, J=8.31 Hz, 1H), 6.13 (s, 1H), 4.50 (d, J=5.65 Hz, 2H), 3.19 (t, J=4.77 Hz, 4H), 3.13 (s, 2H), 2.74 (t, J=4.64 Hz, 4H), 2.27 (s, 3H)

Example 64

Synthesis of 3-{[4-(2-cyanophenyl)piperazin-1-yl]methylcarboxamido}methyl-5-isobutyl-1-phenyl-1H-pyrazole (Compound No. 49)

Title compound was obtained by using the manufacturing method same as in the above Example 15.

Yield: 65.0%

$^1$H NMR (300 MHz, CDCl$_3$) δ 7.72 (br, 1H), 7.52 (d, J=6.25 Hz, 1H), 7.33-7.47 (m, 6H), 6.99 (t, J=7.80 Hz, 1H), 6.87 (d, J=8.35 Hz, 1H), 6.13 (s, 1H), 4.52 (d, J=5.51 Hz, 2H), 3.17-3.19 (m, 4H), 3.13 (s, 2H), 2.74-2.76 (m, 4H), 2.48 (d, J=7.16 Hz, 2H), 1.75-1.84 (m, 1H), 0.85 (s, 3H), 0.82 (s, 3H)

Example 65

Synthesis of 3-{[4-(2,3-dimethylphenyl)piperazin-1-yl]methylcarboxamido}methyl-5-(4-thiomethyl)phenyl-1-phenyl-1H-pyrazole (Compound No. 50)

Title compound was obtained by using the manufacturing method same as in the above Example 15.

Yield: 53.6%

$^1$H NMR (300 MHz, CDCl$_3$) δ 7.93 (br, 1H), 7.28-7.38 (m, 5H), 7.11-7.18 (m, 4H), 7.08 (d, J=7.64 Hz, 1H), 6.92 (d, J=7.49 Hz, 1H), 6.86 (d, J=7.92 Hz, 1H), 6.46 (s, 1H), 4.63 (d,

J=5.65 Hz, 2H), 3.18 (s, 2H), 2.29 (d, J=4.33 Hz, 4H), 2.88 (br, 4H), 2.47 (s, 3H), 2.28 (s, 3H), 2.23 (s, 3H)

Example 66

Synthesis of 3-{[4-(2,4-dimethylphenyl)piperazin-1-yl]methylcarboxamido}methyl-5-(4-thiomethyl)phenyl-1-phenyl-1H-pyrazole (Compound No. 51)

Title compound was obtained by using the manufacturing method same as in the above Example 15.
Yield: 54.4%
$^1$H NMR (300 MHz, CDCl$_3$) δ 7.89 (br, 1H), 7.29-7.36 (m, 5H), 7.12-7.17 (m, 4H), 6.99 (t, J=6.32 Hz, 2H), 6.87 (d, J=7.99 Hz, 1H), 6.45 (s, 1H), 4.62 (d, J=5.67 Hz, 2H), 3.16 (s, 2H), 2.91 (t, J=4.35 Hz, 4H), 2.74 (br, 4H), 2.48 (s, 3H), 2.29 (s, 3H), 2.26 (s, 3H)

Example 67

Synthesis of 3-{[4-(3-hydroxyphenyl)piperazin-1-yl]methylcarboxamido}methyl-5-methyl-1-phenyl-1H-pyrazole (Compound No. 52)

Title compound was obtained by using the manufacturing method same as in the above Example 15.
Yield: 52.0%
$^1$H NMR (300 MHz, CDCl$_3$) δ 7.79 (br, 1H), 7.36-7.44 (m, 5H), 7.01 (t, J=8.06 Hz, 1H), 6.37 (d, J=6.22 Hz, 1H), 6.26-6.30 (m, 2H), 6.18 (s, 1H), 4.53 (d, J=5.76 Hz, 2H), 3.12 (s, 2H), 3.04 (t, J=7.67 Hz, 4H), 2.62 (t, J=4.93 Hz, 4H), 2.29 (s, 3H)

Example 68

Synthesis of 3-{[4-(3-hydroxyphenyl)piperazin-1-yl]methylcarboxamido}methyl-5-isobutyl-1-phenyl-1H-pyrazole (Compound No. 53)

Title compound was obtained by using the manufacturing method same as in the above Example 15.
Yield: 49.3%
$^1$H NMR (300 MHz, CDCl$_3$) δ 7.80 (br, 1H), 7.46-7.35 (m, 5H), 7.01 (t, J=8.04 Hz, 1H), 6.36 (d, J=9.72 Hz, 1H), 6.27-6.29 (m, 2H), 6.15 (s, 1H), 4.52 (d, J=4.29 Hz, 2H), 3.03-3.14 (m, 6H), 2.51-2.67 (m, 4H), 2.47 (d, J=3.74 Hz, 2H), 1.79-1.83 (m, 1H), 0.87 (s, 3H), 0.84 (s, 3H)

Example 69

Synthesis of 3-[(4-phenylpiperazin-1-yl)methylcarboxamido]methyl-5-(4-thiomethyl)phenyl-1-phenyl-1H-pyrazole (Compound No. 54)

Title compound was obtained by using the manufacturing method same as in the above Example 15.
Yield: 62.4%
$^1$H NMR (300 MHz, CDCl$_3$) δ 7.85 (br, 1H), 7.23-7.32 (m, 7H), 7.10-7.16 (m, 4H), 6.88 (d, J=7.62 Hz, 3H), 6.44 (s, 1H), 4.61 (d, J=5.65 Hz, 2H), 3.19 (t, J=4.56 Hz, 4H), 3.15 (s, 2H), 2.72 (t, J=4.90 Hz, 4H), 2.46 (s, 3H)

Example 70

Synthesis of 3-{[4-(3-hydroxyphenyl)piperazin-1-yl]methylcarboxamido}methyl-5-(4-thiomethyl)phenyl-1-phenyl-1H-pyrazole (Compound No. 55)

Title compound was obtained by using the manufacturing method same as in the above Example 15.
Yield: 51.7%
$^1$H NMR (300 MHz, CDCl$_3$) δ 7.87 (br, 1H), 7.25-7.30 (m, 5H), 7.03-7.16 (m, 5H), 6.30-6.45 (m, 4H), 4.60 (d, J=5.69 Hz, 2H), 3.47 (s, 2H), 3.07-3.14 (m, 4H), 2.63-2.69 9 m, 4H), 2.46 (s, 3H)

Example 71

Synthesis of 3-{[4-(2,3-dimethylphenyl)piperazin-1-yl]methylcarboxamido}methyl-5-propyl-1-(4-carboxyl)phenyl-1H-pyrazole (Compound No. 56)

Title compound was obtained by using the manufacturing method same as in the above Example 15.
Yield: 84.7%
$^1$H NMR (300 MHz, CDCl$_3$) δ 7.41-7.49 (m, 4H), 7.08 (t, J=7.62 Hz, 1H), 6.92 (t, J=8.20 Hz, 2H), 6.31 (s, 1H), 5.24 (s, 2H), 3.34 (s, 2H), 2.96 (t, J=4.25 Hz, 4H), 2.79 (br, 4H), 2.61 (t, J=7.48 Hz, 2H), 2.26 (s, 3H), 2.22 (s, 3H), 1.60-1.67 (m, 2H), 0.92 (t, J=3.46 Hz, 3H)

Example 72

Synthesis of 3-{[4-(2,3-dimethylphenyl)piperazin-1-yl]methylcarboxamido}methyl-5-isobutyl-1-(4-carboxy)phenyl-1H-pyrazole (Compound No. 57)

Title compound was obtained by using the manufacturing method same as in the above Example 15.
Yield: 56.8%
$^1$H NMR (300 MHz, CDCl$_3$) δ 7.39-7.61 (m, 4H), 7.08 (s, 1H), 6.92 (t, J=8.58 Hz, 2H), 6.54 (s, 1H), 5.25 (s, 2H), 3.36-3.40 (m, 2H), 2.96-2.97 (m, 4H), 2.79 (br, 4H), 2.52 (d, J=7.11 Hz, 2H), 2.27 (s, 3H), 1.78-1.82 (m, 1H), 0.88 (s, 3H), 0.87 (s, 3H)

Example 73

Synthesis of 3-{[4-(2,3-dimethylphenyl)piperazin-1-yl]methylcarboxamido}methyl-5-methyl-1-(4-carboxy)phenyl-1H-pyrazole (Compound No. 58)

Title compound was obtained by using the manufacturing method same as in the above Example 15.
Yield: 40.0%
$^1$H NMR (300 MHz, CDCl$_3$) δ 7.46 (q, J=6.30 Hz, 4H), 7.08 (t, J=7.64 Hz, 1H), 6.92 (t, J=7.71 Hz, 2H), 6.22 (s, 1H), 4.69 (s, 2H), 3.37 (s, 2H), 2.96 (t, J=4.44 Hz, 4H), 2.79 (br, 4H), 2.33 (s, 3H), 2.27 (s, 3H), 2.23 (s, 3H)

Example 74

Synthesis of 3-{[4-(2,3-dimethylphenyl)piperazin-1-yl]methylcarboxamido}methyl-5-(4-morpholino)phenyl-1-phenyl-1H-pyrazole (Compound No. 59)

Title compound was obtained by using the manufacturing method same as in the above Example 15.
Yield: 42.0%
$^1$H NMR (300 MHz, CDCl$_3$) δ 7.92 (br, 1H), 7.29-7.33 (m, 5H), 7.13 (d, J=8.80 Hz, 2H), 7.07 (d, J=7.70 Hz, 1H), 6.92 (d, J=7.25 Hz, 1H), 6.86 (d, J=7.95 Hz, 1H), 6.80 (d, J=8.81 Hz, 2H), 6.41 (s, 1H), 4.61 (d, J=5.60 Hz, 2H), 3.85 (d, J=4.46 Hz, 4H), 3.17-3.19 (m, 6H), 2.91 (t, J=3.99 Hz, 4H), 2.75 (br, 4H), 2.28 (s, 3H), 2.22 (s, 3H)

Example 75

Synthesis of 3-[(4-phenylpiperazin-1-yl)methylcarboxamido]methyl-5-(4-morpholino)phenyl-1-phenyl-1H-pyrazole (Compound No. 60)

Title compound was obtained by using the manufacturing method same as in the above Example 15.
Yield: 51.6%
$^1$H NMR (300 MHz, CDCl$_3$) δ 7.83 (br, 1H), 7.24-7.30 (m, 7H), 7.11 (d, J=8.84 Hz, 2H), 6.90 (d, J=8.70 Hz, 3H), 6.80 (d, J=8.79 Hz, 2H), 6.39 (s, 1H), 4.60 (d, J=5.63 Hz, 2H), 3.85 (t, J=4.67 Hz, 4H), 3.05-3.21 (m, 10H), 2.73 (t, J=5.01 Hz, 4H)

Example 76

Synthesis of 3-{[4-(2,4-dimethylphenyl)piperazin-1-yl]methylcarboxamido}methyl-5-(4-morpholino)phenyl-1-phenyl-1H-pyrazole (Compound No. 61)

Title compound was obtained by using the manufacturing method same as in the above Example 15.
Yield: 70.0%
$^1$H NMR (300 MHz, CDCl$_3$) δ 7.91 (br, 1H), 7.27-7.34 (m, 5H), 7.11 (d, J=8.80 Hz, 2H), 6.98 (t, J=6.43 Hz, 2H), 6.86 (d, J=8.00 Hz, 1H), 6.80 (d, J=8.81 Hz, 2H), 6.40 (s, 1H), 4.60 (d, J=5.67 Hz, 2H), 3.84 (t, J=4.68 Hz, 4H), 3.15-3.19 (m, 6H), 2.90 (t, J=4.35 Hz, 4H), 2.72 (br, 4H), 2.28 (s, 3H), 2.25 (s, 3H)

Example 77

Synthesis of 3-{[4-(3-trifluorobenzyl)piperazin-1-yl]methylcarboxamido}methyl-5-(4-morpholino)phenyl-1-phenyl-1H-pyrazole (Compound No. 62)

Title compound was obtained by using the manufacturing method same as in the above Example 15.
Yield: 77.5%
$^1$H NMR (300 MHz, CDCl$_3$) δ 7.82 (br, 1H), 7.40-7.53 (m, 3H), 7.32 (d, J=4.37 Hz, 1H), 7.26-7.29 (m, 5H), 7.08 (d, J=8.77 Hz, 2H), 6.77 (d, J=8.79 Hz, 2H), 6.36 (s, 1H), 4.54 (d, J=5.75 Hz, 2H), 3.82 (t, J=4.60 Hz, 4H), 3.51 (s, 2H), 3.14 (t, J=4.80 Hz, 4H), 3.07 (s, 2H), 2.58 (br, 4H), 2.46 (br, 4H)

Example 78

Synthesis of 3-{[4-(4-trifluorobenzyl)piperazin-1-yl]methylcarboxamido}methyl-5-(4-morpholino)phenyl-1-phenyl-1H-pyrazole (Compound No. 63)

Title compound was obtained by using the manufacturing method same as in the above Example 15.
Yield: 41.3%
$^1$H NMR (300 MHz, CDCl$_3$) δ 7.77 (br, 1H), 7.56 (d, J=8.05 Hz, 2H), 7.42 (d, J=8.02 Hz, 2H), 7.27-7.33 (m, 5H), 7.10 (d, J=6.97 Hz, 2H), 6.80 (d, J=8.88 Hz, 2H), 6.37 (s, 1H), 4.57 (d, J=5.77 Hz, 2H), 3.84 (t, J=4.72 Hz, 4H), 3.53 (s, 2H), 3.17 (t, J=4.90 Hz, 4H), 3.08 (s, 2H), 2.59 (br, 4H), 2.46 (br, 4H)

Example 79

Synthesis of 3-{[4-(2,3-dimethylphenyl)piperazin-1-yl]carbonylmethylamino}methyl-5-methyl-1-phenyl-1H-pyrazole (Compound No. 64)

1-Chloroacetyl-4-(2,3-dimethylphenyl)piperazine (0.072 g, 0.3 mmol) and K$_2$CO$_3$ (0.062 g, 0.45 mmol) were dissolved in 5 mL of purified acetonitrile and stirred at 50° C. for about 30 minutes. Then, the reaction mixture was dropwisely added with 3-aminomethyl-5-methyl-1-phenylpyrazole (0.056 g, 0.3 mmol) and stirred at 80° C. Completion of the reaction was confirmed by TLC (ethyl acetate). Upon completion, the reaction mixture was added with water and then extracted with methylene chloride. The resulting organic layer was dried with anhydrous magnesium sulfate and filtered, and the filtrate was concentrated under reduced pressure and purified by column chromatography (ethyl acetate) to obtain the title compound.
Yield: 30.2%
$^1$H NMR (300 MHz, CDCl$_3$) δ 7.36-7.47 (m, 5H), 7.05-7.08 (m, 1H), 6.93-6.95 (m, 1H), 6.84-6.87 (m, 1H), 6.22 (s, 1H), 3.90 (s, 3H), 3.56 (s, 4H), 2.85 (t, J=4.76 Hz, 4H), 2.34 (br, 2H), 2.32 (s, 3H), 2.28 (s, 3H), 2.24 (s, 3H)

Example 80

Synthesis of 3-[(4-benzhydrylpiperazin-1-yl)carbonylmethylamino]methyl-5-methyl-1-phenyl-1H-pyrazole (Compound No. 65)

Title compound was obtained by using the manufacturing method same as in the above Example 79.
Yield: 35.4%
$^1$H NMR (300 MHz, CDCl$_3$) δ 7.19-7.43 (m, 15H), 6.21 (s, 1H), 3.89 (s, 2H), 3.79 (t, J=4.79 Hz, 2H), 3.53-3.56 (m, 4H), 3.15-3.19 (m, 6H), 2.32 (s, 3H)

Example 81

Synthesis of 3-[(4-phenylpiperazin-1-yl)carbonylmethylamino]methyl-5-methyl-1-phenyl-1H-pyrazole (Compound No. 66)

Title compound was obtained by using the manufacturing method same as in the above Example 79.
Yield: 23.1%
$^1$H NMR (300 MHz, CDCl$_3$) δ 7.36-7.46 (m, 5H), 7.25-7.30 (m, 2H), 6.90-6.93 (m, 3H), 6.21 (s, 1H), 3.89 (s, 2H), 3.79 (t, J=4.79 Hz, 2H), 3.53-3.56 (m, 4H), 3.15-3.19 (m, 6H), 2.32 (s, 3H)

Example 82

Synthesis of 3-[(4-phenylpiperazin-1-yl)carbonylmethylamino]methyl-5-isobutyl-1-phenyl-1H-pyrazole (Compound No. 67)

Title compound was obtained by using the manufacturing method same as in the above Example 79.
Yield: 35.7%
$^1$H NMR (300 MHz, CDCl$_3$) δ 7.27-7.46 (m, 5H), 6.89-6.93 (m, 5H), 6.30 (s, 1H), 3.84 (s, 2H), 3.77-3.80 (m, 4H), 3.55 (s, 2H), 3.15-3.16 (m, 4H), 2.50 (d, J=7.18 Hz, 2H), 1.78-1.83 (m, 1H), 0.85 (s, 3H), 0.83 (s, 3H)

Example 83

Synthesis of 3-[(4-benzhydrylpiperazin-1-yl)carbonylmethylamino]methyl-5-isobutyl-1-phenyl-1H-pyrazole (Compound No. 68)

Title compound was obtained by using the manufacturing method same as in the above Example 79.
Yield: 41.3%
$^1$H NMR (300 MHz, CDCl$_3$) δ 7.40-7.45 (m, 5H), 7.27-7.39 (m, 7H), 7.18-7.23 (m, 3H), 6.25 (s, 1H), 4.17 (s, 2H), 3.75 (s, 2H), 3.57 (br, 4H), 3.41 (s, 2H), 2.44 (d, J=7.16 Hz, 2H), 2.34 (br, 4H), 1.70-1.74 (m, 1H), 0.87 (s, 3H), 0.83 (s, 3H)

Example 84

Synthesis of 3-{[4-(2,4-dimethylphenyl)piperazin-1-yl]carbonylmethylamino}methyl-5-isobutyl-1-phenyl-1H-pyrazole (Compound No. 69)

Title compound was obtained by using the manufacturing method same as in the above Example 79.
Yield: 9.3%
$^1$H NMR (300 MHz, CDCl$_3$) δ 7.38-7.46 (m, 5H), 6.97-7.02 (m, 2H), 6.85-6.88 (m, 2H), 6.23 (s, 1H), 3.90 (s, 2H), 3.77 (br, 2H), 3.48-3.55 (m, 4H), 2.84 (t, J=4.70 Hz, 4H), 2.51 (d, J=7.16 Hz, 2H), 2.28 (s, 6H), 1.80-1.85 (m, 1H), 0.88 (s, 3H), 0.86 (s, 3H)

Example 85

Synthesis of 3-[(4-phenylpiperazin-1-yl)carbonylmethylamino]methyl-5-furyl-1-phenyl-1H-pyrazole (Compound No. 70)

Title compound was obtained by using the manufacturing method same as in the above Example 79.
Yield: 40.2%
$^1$H NMR (300 MHz, CDCl$_3$) δ 7.37-7.45 (m, 2H), 7.27 (t, J=8.77 Hz, 3H), 6.88-6.93 (m, 5H), 6.76 (s, 1H), 6.32-6.34 (m, 1H), 5.97 (d, J=3.39 Hz, 1H), 3.91 (s, 2H), 3.78 (br, 4H), 3.60 (s, 2H), 3.15-3.16 (m, 4H)

Example 86

Synthesis of 3-[(4-benzhydrylpiperazin-1-yl)carbonylmethylamino]methyl-5-furyl-1-phenyl-1H-pyrazole (Compound No. 71)

Title compound was obtained by using the manufacturing method same as in the above Example 79.
Yield: 26.4%
$^1$H NMR (300 MHz, CDCl$_3$) δ 7.38-7.40 (m, 6H), 7.26-7.33 (m, 6H), 7.17-7.22 (m, 4H), 6.72 (s, 1H), 6.34-6.35 (m, 1H), 5.94 (d, J=3.36 Hz, 1H), 4.18 (s, 2H), 3.83 (s, 1H), 3.59 (br, 4H), 3.46 (br, 2H), 2.35 (br, 4H)

Example 87

Synthesis of 3-{[4-(2,4-dimethyl)phenylpiperazin-1-yl]carbonylmethylamino}methyl-5-furyl-1-phenyl-1H-pyrazole (Compound No. 72)

Title compound was obtained by using the manufacturing method same as in the above Example 79.
Yield: 17.0%
$^1$H NMR (300 MHz, CDCl$_3$) δ 7.39-7.45 (m, 6H), 6.99 (t, J=9.47 Hz, 2H), 6.87 (d, J=8.01 Hz, 1H), 6.68 (s, 1H), 6.32-6.34 (br, 2H), 5.99 (d, J=3.37 Hz, 1H), 3.96 (s, 2H), 3.78 (br, 2H), 3.57 (s, 2H), 3.53 (br, 2H), 2.85 (t, J=4.89 Hz, 4H), 2.28 (s, 6H)

Example 88

Synthesis of 3-{[4-(2,4-dimethyl)phenylpiperazin-1-yl]carbonylmethylamino}methyl-5-methyl-1-phenyl-1H-pyrazole (Compound No. 73)

Title compound was obtained by using the manufacturing method same as in the above Example 79.
Yield: 36.6%
$^1$H NMR (300 MHz, CDCl$_3$) δ 7.37-7.47 (m, 5H), 7.02 (s, 1H), 6.97 (d, J=8.30 Hz, 1H), 6.86 (d, J=8.03 Hz, 1H), 6.34 (s, 1H), 3.76 (br, 4H), 3.56 (s, 2H), 3.47 (s, 2H), 2.85 (br, 4H), 2.33 (s, 3H), 2.29 (s, 6H)

Example 89

Synthesis of 3-{[4-(3,4-dichloro)benzylpiperazin-1-yl]carbonylmethylamino}methyl-5-methyl-1-phenyl-1H-pyrazole (Compound No. 74)

Title compound was obtained by using the manufacturing method same as in the above Example 79.
Yield: 30.2%
$^1$H NMR (300 MHz, CDCl$_3$) δ 7.34-7.48 (m, 71-1), 7.13 (d, J=8.75 Hz, 1H), 6.27 (s, 1H), 3.61 (br, 4H), 3.48 (s, 2H), 3.46 (s, 2H), 3.42 (s, 2H), 2.39 (br, 4H), 2.32 (s, 3H)

Example 90

Synthesis of 3-{[4-(3,4-dichlorobenzyl)piperazin-1-yl]carbonylmethylamino}methyl-5-isobutyl-1-phenyl-1H-pyrazole (Compound No. 75)

Title compound was obtained by using the manufacturing method same as in the above Example 79.
Yield: 10.1%
$^1$H NMR (300 MHz, CDCl$_3$) δ 7.35-7.48 (m, 7H), 7.13-7.16 (m, 1H), 6.20 (s, 1H), 3.87 (s, 2H), (t, J=4.46, 2H), 3.49 (s, 2H), 3.44 (s, 2H), 3.39 (t, J=4.54, 2H), 2.50 (d, J=7.14, 2H), 2.40 (br, 4H), 1.79-1.84 (m, 1H), 0.87 (s, 3H)

Example 91

Synthesis of 3-{[4-(2,3-dimethylphenyl)piperazin-1-yl]carbonylmethylamino}methyl-5-isobutyl-1-phenyl-1H-pyrazole (Compound No. 76)

Title compound was obtained by using the manufacturing method same as in the above Example 79.
Yield: 18.6%
$^1$H NMR (300 MHz, CDCl$_3$) δ 7.38-7.49 (m, 5H), 7.06 (t, J=3.86 Hz, 1H), 6.93 (d, J=7.29 Hz, 1H), 6.85 (d, J=7.85 Hz, 1H), 6.23 (s, 1H), 3.91 (s, 2H), 3.56 (br, 4H), 2.83-2.86 (m, 4H), 2.52 (d, J=7.16 Hz, 2H), 2.28 (s, 3H), 2.24 (s, 3H), 1.82-1.86 (m, 1H), 0.89 (s, 3H), 0.87 (s, 3H)

Example 92

Synthesis of 3-{[4-(2,3-dimethylphenyl)piperazin-1-yl]carbonylmethylamino}methyl-5-furyl-1-phenyl-1H-pyrazole (Compound No. 77)

Title compound was obtained by using the manufacturing method same as in the above Example 79.
Yield: 29.8%
$^1$H NMR (300 MHz, CDCl$_3$) δ 7.38-7.43 (m, 5H), 7.06 (t, J=7.57, 1H), 6.93 (d, J=7.31, 1H), 6.83 (t, J=7.91, 2H), 6.33 (t, J=1.56, 1H), 5.99 (d, J=3.27, 1H), 3.94 (s, 2H), 3.76 (br, 4H), 3.61 (s, 2H), 2.87 (br, 4H), 2.28 (s, 3H), 2.23 (s, 3H)

Example 93

Synthesis of 3-{[4-(3,4-dichlorobenzyl)piperazin-1-yl]carbonylmethylamino}methyl-5-furyl-1-phenyl-1H-pyrazole (Compound No. 78)

Title compound was obtained by using the manufacturing method same as in the above Example 79.

Yield: 22.8%
$^1$H NMR (300 MHz, CDCl$_3$) δ 7.34-7.43 (m, 7H), 7.13 (d, J=6.40, 2H), 6.73 (s, 1H), 6.33-6.34 (m, 1H), 5.96-5.97 (m, 1H), 3.85 (s, 2H), 3.61 (br, 4H), 3.50 (s, 2H), 3.41 (br, 4H), 2.38 (t, J=6.40, 4H)

Example 94

Synthesis of 3-[(4-piperonylpiperazin-1-yl)carbonyl-methylamino]methyl-5-isobutyl-1-phenyl-1H-pyrazole (Compound No. 79)

Title compound was obtained by using the manufacturing method same as in the above Example 79.
Yield: 58.8%
$^1$H NMR (300 MHz, CDCl$_3$) δ 7.29-7.43 (m, 5H), 6.69-6.80 (m, 3H), 6.23 (s, 1H), 5.91 (s, 2H), 3.74 (s, 2H), 3.54 (br, 4H), 3.44 (s, 2H), 3.36 (s, 2H), 2.45 (d, J=7.16, 2H), 2.35 (br, 4H), 1.83-1.88 (m, 1H), 0.82 (s, 3H), 0.79 (s, 3H)

Example 95

Synthesis of 3-[(4-piperonylpiperazin-1-yl)carbonyl-methylamino]methyl-5-furyl-1-phenyl-1H-pyrazole (Compound No. 80)

Title compound was obtained by using the manufacturing method same as in the above Example 79.
Yield: 30.2%
$^1$H NMR (300 MHz, CDCl$_3$) δ 7.37-7.45 (m, 5H), 6.83 (s, 2H), 6.72-6.76 (m, 4H), 6.34 (d, J=1.61, 1H), 5.97 (d, J=3.46, 1H), 3.84 (s, 2H), 3.60 (br, 4H), 3.48 (s, 2H), 2.32 (br, 4H)

Example 96

Synthesis of 3-{[4-(2,3,4-trimethoxybenzyl)piperazin-1-yl]carbonylmethylamino}methyl-5-isobutyl-1-phenyl-1H-pyrazole (Compound No. 81)

Title compound was obtained by using the manufacturing method same as in the above Example 79.
Yield: 40.0%
$^1$H NMR (300 MHz, CDCl$_3$) δ 7.33-7.45 (m, 5H), 6.95 (d, J=8.49, 1H), 6.63 (d, J=8.58, 1H), 6.29 (s, 1H), 3.87 (s, 6H), 3.85 (s, 3H), 3.57 (br, 4H), 3.45 (s, 6H), 2.49 (d, J=7.14, 2H), 2.41 (br, 4H), 1.84-1.90 (m, 1H), 0.85 (s, 3H), 0.83 (s, 3H)

Example 97

Synthesis of 3-{[4-(2,3-dimethylphenyl)piperazin-1-yl]carbonylmethylamino}methyl-5-propyl-1-phenyl-1H-pyrazole (Compound No. 82)

Title compound was obtained by using the manufacturing method same as in the above Example 79.
Yield: 22.4%
$^1$H NMR (300 MHz, CDCl$_3$) δ 7.38-7.46 (m, 5H), 7.07 (t, J=7.70, 1H), 6.94 (d, J=7.31, 1H), 6.84 (d, J=7.66, 1H), 6.35 (s, 1H), 3.70-3.86 (m, 6H), 3.57 (s, 2H), 2.86 (br, 4H), 2.61 (t, J=7.53, 2H), 2.28 (s, 3H), 2.18 (s, 3H), 1.58-1.63 (m, 2H), 0.92 (t, J=7.28, 3H)

Example 98

Synthesis of 3-{[4-(2,4-dimethylphenyl)piperazin-1-yl]carbonylmethylamino}methyl-5-propyl-1-phenyl-1H-pyrazole (Compound No. 83)

Title compound was obtained by using the manufacturing method same as in the above Example 79.
Yield: 36.6%
$^1$H NMR (300 MHz, CDCl$_3$) δ 7.38-7.47 (m, 5H), 7.03 (s, 1H), 6.96 (d, J=8.20, 1H), 6.86 (d, J=7.92, 1H), 6.36 (s, 1H), 3.86 (s, 2H), 3.82 (br, 4H), 3.57 (s, 2H), 2.85 (br, 4H), 2.61 (t, J=7.67, 2H), 2.29 (s, 6H), 1.59-1.66 (m, 2H), 0.93 (t, J=6.65, 3H)

Example 99

Synthesis of 3-[(4-phenylpiperazin-1-yl)carbonylmethylamino]methyl-5-propyl-1-phenyl-1H-pyrazole (Compound No. 84)

Title compound was obtained by using the manufacturing method same as in the above Example 79.
Yield: 41.0%.
$^1$H NMR (300 MHz, CDCl$_3$) δ 7.37-7.44 (m, 5H), 7.25-7.30 (m, 2H), 6.88-6.93 (m, 3H), 6.30 (s, 1H), 3.83 (s, 2H), 3.71-3.78 (m, 4H), 3.55 (s, 2H), 3.09-3.16 (m, 4H), 2.59 (t, J=7.53, 2H), 1.55-1.63 (m, 2H), 0.90 (t, J=7.31, 3H)

Example 100

Synthesis of 3-[(4-phenylpiperazin-1-yl)methylcarboxamido]methyl-5-methyl-1-[(4-methoxy)phenyl]-1H-pyrazole (Compound No. 85)

Title compound was obtained by using the manufacturing method same as in the above Example 15.
Yield: 45.0%
$^1$H NMR (300 MHz, CDCl$_3$) δ 7.74 (br, 1H), 7.23-7.32 (m, 4H), 6.84-6.94 (m, 5H), 6.11 (s, 1H), 4.51 (d, J=5.56 Hz, 2H), 3.82 (s, 3H), 3.17 (t, J=4.76 Hz, 3H), 3.12 (s, 3H), 2.70 (t, J=5.04 Hz, 4H), 2.26 (s, 3H)

Example 101

Synthesis of 3-[(4-phenylpiperazin-1-yl)methylcarboxamido]methyl-5-[(4-piperidino)phenyl]-1-phenyl-1Hpyrazole (Compound No. 86)

Title compound was obtained by using the manufacturing method same as in the above Example 15.
Yield: 63.2%
$^1$H NMR (300 MHz, CDCl$_3$) δ 7.84 (br, 1H), 7.24-7.32 (m, 8H), 7.08 (d, J=8.81 Hz, 2H), 6.91-6.80 (m, 4H), 6.38 (s, 1H), 4.61 (d, J=7.39 Hz, 2H), 3.17-3.19 (m, 8H), 3.16 (s, 2H), 2.73 (d, J=5.00 Hz, 4H), 1.67-1.73 (m, 4H), 1.59-1.62 (m, 2H)

Example 102

Synthesis of 3-[(4-phenylpiperazin-1-yl)methylcarboxamido]methyl-5-isobutyl-1-[(4-methoxy)phenyl]-1H-pyrazole (Compound No. 87)

Title compound was obtained by using the manufacturing method same as in the above Example 15.
Yield: 50.2%
$^1$H NMR (300 MHz, CDCl$_3$) δ 7.73 (br, 1H), 7.23-7.28 (m, 4H), 6.86-6.95 (m, 5H), 6.11 (s, 1H), 4.53 (d, J=5.54 Hz, 2H), 3.82 (s, 3H), 3.16 (t, J=4.45 Hz, 4H), 3.12 (s, 3H), 2.70 (t, J=4.83 Hz, 4H), 2.46 (d, J=7.20 Hz, 2H), 1.77-1.82 (m, 1H), 0.86 (s, 3H), 0.82 (s, 3H)

Example 103

Synthesis of 3-{(4-(2,3-dimethylphenyl)piperazin-1-yl]methylcarboxamido}methyl-5-isobutyl-1-[(4-methoxy)phenyl]-1H-pyrazole (Compound No. 88)

Title compound was obtained by using the manufacturing method same as in the above Example 15.
Yield: 48.5%
$^1$H NMR (300 MHz, CDCl$_3$) δ 7.82 (br, 1H), 7.27-7.31 (m, 2H), 7.07 (t, J=7.68 Hz, 1H), 6.90-6.97 (m, 3H), 6.82 (d, J=7.89 Hz, 1H), 6.12 (s, 1H), 4.54 (d, J=5.60 Hz, 2H), 3.82 (s, 3H), 3.14 (s, 2H), 2.87 (t, J=4.44 Hz, 4H), 2.71 (br, 4H, 2.46 (d, J=7.19 Hz, 2H), 2.22 (s, 3H), 2.20 (s, 3H), 1.78-1.83 (m, 1H), 0.87 (s, 3H), 0.83 (s, 3H)

Example 104

Synthesis of 3-[(4-phenylpiperazin-1-yl)methylcarboxamido]methyl-5-(2-pyridyl)-1-phenyl-1H-pyrazole (Compound No. 89)

Title compound was obtained by using the manufacturing method same as in the above Example 15.
Yield: 56.0%
$^1$H NMR (300 MHz, CDCl$_3$) δ 8.56-8.58 (m, 1H), 7.75 (br, 1H), 7.59-7.61 (m, 1H), 7.17-7.33 (m, 10H), 6.87-6.91 (m, 2H), 6.74 (s, 1H), 4.63 (d, J=5.63 Hz, 2H), 3.19 (t, J=4.81 Hz, 4H), 3.15 (s, 2H), 2.73 (t, J=5.06 Hz, 4H)

Example 105

Synthesis of 3-{(4-(2,3-dimethylphenyl)piperazin-1-yl]methylcarboxamido}methyl-5-(2-pyridyl)-1-phenyl-1H-pyrazole (Compound No. 90)

Title compound was obtained by using the manufacturing method same as in the above Example 15.
Yield: 63.5%
$^1$H NMR (300 MHz, CDCl$_3$) δ8.57 (d, J=3.38 Hz, 1H), 7.88 (br, 1H), 7.61 (t, J=1.99 Hz, 1H), 7.30-7.35 (m, 5H), 7.16-7.22 (m, 2H), 7.06 (t, J=7.70 Hz, 1H), 6.85-6.93 (m, 2H), 6.75 (s, 1H), 4.64 (d, J=5.63 Hz, 2H), 3.17 (s, 2H), 2.90 (t, J=4.54 Hz, 4H), 2.74 (br, 4H), 2.27 (s, 3H), 2.21 (s, 3H)

Example 106

Synthesis of 3-[(4-phenylpiperazin-1-yl)methylcarboxamido]methyl-5-[(4-methyl)phenyl]-1-phenyl-1H-pyrazole (Compound No. 91)

Title compound was obtained by using the manufacturing method same as in the above Example 15.
Yield: 58.6%
$^1$H NMR (300 MHz, CDCl$_3$) δ 7.86 (br, 1H), 7.25-7.33 (m, 7H), 7.09-7.11 (m, 4H), 6.86-6.91 (m, 3H), 6.44 (s, 1H), 4.62 (d, J=5.65 Hz, 2H), 3.20 (t, J=4.77 Hz, 4H), 3.16 (s, 2H), 2.74 (t, J=5.01 Hz, 4H), 2.35 (s, 3H)

Example 107

Synthesis of 3-{(4-(2,3-dimethylphenyl)piperazin-1-yl]methylcarboxamido}methyl-5-[(4-methyl)phenyl]-1-phenyl-1H-pyrazole (Compound No. 92)

Title compound was obtained by using the manufacturing method same as in the above Example 15.
Yield: 70.2%
$^1$H NMR (300 MHz, CDCl$_3$) δ 7.96 (br, 1H), 7.29-7.34 (m, 5H), 7.06-7.12 (m, 5H), 6.92 (d, J=7.30 Hz, 1H), 6.87 (d, J=7.92 Hz, 1H), 6.45 (s, 1H), 4.63 (d, J=5.66 Hz, 2H), 3.18 (s, 2H), 2.92 (t, J=4.43 Hz, 4H), 2.75 (br, 4H), 2.35 (s, 3H), 2.29 (s, 3H), 2.22 (s, 3H)

Example 108

Synthesis of 3-[(4-phenylpiperazin-1-yl)methylcarboxamido]methyl-5-methyl-1-benzyl-1H-pyrazole (Compound No. 93)

Title compound was obtained by using the manufacturing method same as in the above Example 15.
Yield: 58.9%
$^1$H NMR (300 MHz, CDCl$_3$) δ7.69 (br, 1H), 7.23-7.30 (m, 5H), 7.03-7.06 (m, 2H), 6.67-6.90 (m, 3H), 6.01 (s, 1H), 5.22 (s, 2H), 4.47 (d, J=5.51 Hz, 2H), 3.14 (t, J=4.85 Hz, 4H), 3.07 (s, 2H), 2.68 (t, J=5.12 Hz, 4H), 2.19 (s, 3H)

Example 109

Synthesis of 3-{(4-(2,3-dimethylphenyl)piperazin-1-yl]methylcarboxamido}methyl-5-methyl-1-benzyl-1H-pyrazole (Compound No. 94)

Title compound was obtained by using the manufacturing method same as in the above Example 15.
Yield: 74.2%
$^1$H NMR (300 MHz, CDCl$_3$) δ 7.73 (br, 1H), 7.24-7.33 (m, 3H), 7.07 (t, J=6.82 Hz, 3H), 6.92 (d, J=7.32 Hz, 1H), 6.84 (d, J=7.92 Hz, 1H), 6.02 (s, 1H), 5.26 (s, 2H), 4.48 (d, J=5.62 Hz, 2H), 3.14 (s, 2H), 2.86 (t, J=4.47 Hz, 4H), 2.70 (br, 4H), 2.27 (s, 3H), 2.20 (s, 3H), 2.16 (s, 3H)

FORMULATION EXAMPLES

The novel compound of the present invention represented by the above formula 1 can be formulated into various types depending on the purposes. The followings described a few exemplary formulations which comprise the compound represented by the above formula 1 as an active ingredient and should not be construed as limiting the scope of the present invention.

Formulation Example 1

Tablets (Direct Pressure)

After sieving 5.0 mg of the active ingredient, it was mixed with 14.1 mg of lactose, 0.8 mg of crospovidone USNF and 0.1 mg of magnesium stearate and prepared into a tablet by pressuring.

Formulation Example 2

Tablets (Wet Granulation)

After sieving 5.0 mg of the active ingredient, it was mixed with 16.0 mg of lactose and 4.0 mg of starch. The mixture was added with 0.3 mg of polysorbate 80, which was dissolved in distilled water, for granulation. The resultant granulate was dried, sieved and then mixed with 2.7 mg of colloidal silicon dioxide and 2.0 mg of magnesium stearate. The granulate was prepared into a tablet by pressuring.

Formulation Example 3

Powder and Capsules

After sieving 5.0 mg of the active ingredient, it was mixed with 14.8 mg of lactose, 10.0 mg of polyvinyl pyrrolidone and 0.2 mg of magnesium stearate. The mixture was filled into a hard No. 5 gelatin capsule by using a suitable device.

Formulation Example 4

Injections

Injection was prepared so that it can comprise 100 mg of the active ingredient, 180 mg of mannitol, 26 mg of $Na_2HPO_4 \cdot 12H_2O$ and 2,974 mg of distilled water.

TEST EXAMPLE

The novel compounds of the present invention represented by the above formula 1 were tested for their antagonistic activities with regard to T-type calcium channel as follows. First, as a primary screening, of the above synthesized compounds, those which showed more than 40% of inhibition against T-type calcium channel were selected by using a HTS device FDSS6000, and their $IC_{50}$ values were determined by measuring the electric potential of $Ca^{2+}$ for the human HEK 293 cells.

1) Method of Screening Activity in Relation with T-Type Calcium Channel by Using FDSS6000

Twelve to twenty four hours prior to conducting an activity test, HEK293 cell line (α1G cell line: KCTC 10519BP, KRIBB (Korea Research Institute of Bioscience and Biotechnology) GENE BANK), wherein both α1G T-type calcium channel and Kir2.1 are well expressed, was subcultured into a poly-L-lysine treated 96-well plate to a concentration of $4 \times 10^4$/well by using a 96-well cell distributor (Titertek). On the test day, the cells adhered to the 96-well plate were washed three times with HEPES buffer solution (150 mM NaCl, 5 mM KCl, 1 mM $MgCl_2$, 2 mM $CaCl_2$, 10 mM HEPES, 10 mM glucose, pH 7.4) by using a 96-well plate automatic washer (Bio Tek) and reacted at room temperature with HEPES buffer solution containing 5 μM fluo-3/AM and 0.001% Pluronic F-127 for 1 hour, labeled with a fluorescent dye and then washed twice with HEPES buffer solution. Then, 10 minutes prior to the test by using FDSS6000, the cells were washed once with HEPES buffer solution containing 10 mM $CaCl_2$, and then the final volume was adjusted to 81 μL. Apart from the above-mentioned 96-well plate with cells, two additional 96-well plates, one containing KCl (final concentration of 75 mM) for the activation of T-type calcium channel and another containing a blocking agent of T-type calcium channel were prepared.

Considering that most cell-based HTS devices only provide a liquid application system for drug injection but not a liquid absorption system, 27 μL each of the above-mentioned KCl and blocking agent was prepared respectively in HEPES buffer solution with 5 times as high as that of their respective normal concentration, diluted in the final volume of 135 μL (1/5 dilution) of the cell plate and cell activity was measured.

For FDSS6000 measurements, after the 20-sec baseline recordings cells were pretreated with drugs for 75 seconds and the change in intracellular calcium concentration induced by KCl was measured. The percent inhibition by a test compound was calculated as integrated values of 340/380 fluorescent ratio of untreated and drug-treated cells. The control drug was 10 μM of Mibefradil®.

In details, cells were selectively exposed to 340 nm and 380 nm light excited by xenon lamps installed in FDSS6000 using a computer-controlled filter wheel. The emitter fluorescence light through a 515 nm long-pass filter was passed by a freezing digital CCD camera mounted on the device. Data were collected every 1.23 seconds, and an average value of 340/380 fluorescent ratio for each well was obtained using a digital fluorescent analyzer. Data acquisition and analysis were performed using a program provided by Hamamatsu Photonics.

2) Methods for the Measurements of T-Type Calcium Channel Activity Using an Electrophysiological Whole-Cell Patch-Clamp Technique HEK293 cells stably expressing T-type calcium channels were cultured in DMEM (Dulbecco's modified Eagle's medium) containing 10% (v/v) fetal bovine serum and 1% penicillin/streptomycin (v/v) in humidified 5% $CO_2$ at 36.5° C. Cells expressing $α_{1G}$ T-type calcium channels were selected using G-418 (0.5 mg/mL) in the culture medium. The culture medium was replaced with a fresh one every 3-4 days, and cells were subcultured every week.

Cells were seeded on the coverglass coated with poly-L-lysine (0.5 mg/mL) for the measurements of T-type calcium channel activity 2-7 days prior to the recordings. Whole-cell recordings of T-type calcium channel currents were performed using an EPC-9 patch clamp amplifier (HEKA, Germany). Whole-cell currents were recorded using micropipettes with resistance of 3-4MΩ with the pipette (intracellular) solution containing (in mM): 130 KCl, 11 EGTA, 5 Mg-ATP, and 10 HEPES, pH to 7.4 and with the bath (extracellular) solution containing (in mM): 140 NaCl, 2 $CaCl_2$, and 10 HEPES, pH to 7.4. The inward currents of T-type calcium channels were evoked by the test pulses of −30 mV for 50 ms at a holding potential of −100 mV every 10 seconds.

Each compound was dissolved in dimethylsulfoxide (DMSO) as 10 mM stock solutions and diluted in the bath solution to 10 μM (containing 0.1% DMSO). The initial test was performed to find the range of drug concentrations that exhibits the inhibition effects, in which 1050 values were obtained (mostly in the range of 0.1-100 μM). More specifically, each compound was perfused to the bath for about 30-60 seconds, and the inhibition of the inward peak currents by a test compound was calculated as a percent inhibition from which $IC_{50}$ values were determined. The results are shown in the Table 2.

TABLE 2

| Test compound | $IC_{50}$ (α1G), μM |
|---|---|
| Compound No. 1 | 0.02 ± 0.01 |
| Compound No. 3 | 1.83 ± 0.12 |
| Compound No. 5 | 1.42 ± 0.16 |
| Compound No. 6 | 1.42 ± 0.16 |

TABLE 2-continued

| Test compound | IC$_{50}$ ($\alpha$1G), μM |
|---|---|
| Compound No. 9 | 3.54 ± 0.09 |
| Compound No. 11 | 2.57 ± 0.17 |
| Compound No. 16 | 1.77 ± 0.10 |
| Compound No. 27 | 5.10 ± 0.11 |
| Compound No. 32 | 1.81 ± 0.09 |
| Compound No. 33 | 9.56 ± 1.42 |
| Compound No. 36 | 9.42 ± 0.70 |
| Compound No. 64 | 2.06 ± 1.2 |
| Compound No. 65 | 3.5 ± 0.35 |
| Compound No. 69 | 0.40 ± 0.04 |
| Compound No. 75 | 0.30 ± 0.01 |
| Compound No. 76 | 0.36 ± 0.03 |

INDUSTRIAL APPLICABILITY

As stated above, the pyrazolylmethylamine-piperazine derivatives or their pharmaceutically acceptable salts thereof of the present invention represented by the above formula 1 exhibit excellent activity as an antagonist of T-type calcium channel, and are thus useful for the prevention and treatment of cerebral diseases, cardiovascular diseases, and pain-related diseases.

More specifically, the compounds of the present invention are shown to effectively block the T-type calcium channel, and are thus expected to be useful for the prevention and treatment of cerebral diseases such as epilepsy, depression, Parkinson's disease, dementia, sleep disorder; cardiovascular diseases such as hypertension, cardiac arrhythmia, angina pectoris, myocardial infarction and congestive heart failure; pain-related diseases such as neuropathic pain, chronic pain and acute pain.

The invention claimed is:

1. A compound selected from the group consisting of pyrazolylmethylamine-piperazine derivatives represented by the following formula 1 and their pharmaceutically acceptable salts thereof,

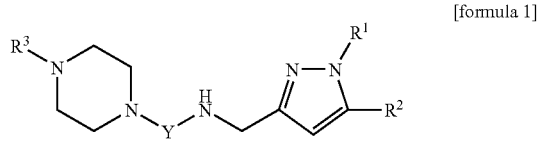

[formula 1]

wherein

Y represents —(CH$_2$)$_n$—C(O)—; or —C(O)—(CH$_2$)$_n$—, wherein n is an integer of 1-4;

R$^1$ and R$^2$, which may be same or different, respectively represent a hydrogen atom; C$_1$-C$_8$ alkyl group; phenyl group; phenyl group substituted with at least one substituent selected from the group consisting of halo, hydroxy, carboxy, carboalkoxy, nitro, cyano, amino, mercapto, thioalkyl, C$_1$-C$_8$ alkyl, C$_1$-C$_8$ cycloalkyl, C$_1$-C$_8$ haloalkyl, C$_1$-C$_8$ alkoxy groups, and C$_3$-C$_8$ heterocycloalkyl group comprising at least one heteroatom selected from O, S, and N; benzyl group; benzyl group substituted with at least one substituent selected from the group consisting of halo, hydroxy, carboxyl, carboalkoxy, nitro, cyano, amino, mercapto, thioalkyl, C$_1$-C$_8$ alkyl, C$_1$-C$_8$ haloalkyl, C$_1$-C$_8$ alkoxy groups, and 5-7 membered heterocycloalkyl groups comprising at least one heteroatom selected from O, S and N; phenethyl group; or heteroaryl group comprising at least one heteroatom selected from O, S and N, wherein the heteroaryl group is selected from furyl, pyridyl, pyrimidyl, and piperonyl groups; and R$^3$ represents a hydrogen atom; C$_1$-C$_8$ alkyl group; heteroaryl group comprising at least one heteroatom selected from O, S and N, wherein the heteroaryl group is selected from furyl, pyridyl, pyrimidyl, and piperonyl groups; phenyl group; phenyl group substituted with at least one substituent selected from the group consisting of halo, hydroxy, carboxy, carboalkoxy, nitro, cyano, amino, mercapto, thioalkyl, C$_1$-C$_8$ alkyl, C$_1$-C$_8$ haloalkyl, C$_1$-C$_8$ cycloalkyl, C$_1$-C$_8$ alkoxy groups, and C$_3$-C$_8$ heterocycloalkyl group comprising at least one heteroatom selected from O, S, and N; benzyl group; benzyl group substituted with at least one substituent selected from the group consisting of halo, hydroxy, carboxy, carboalkoxy, nitro, cyano, amino, mercapto, aryl, haloaryl, thioalkyl, C$_1$-C$_8$ alkyl, C$_1$-C$_8$ alkoxy, C$_1$-C$_8$ haloalkyl, arylcarbonyl, phenyl, and benzyl groups, and 5-7 membered heterocycloalkyl groups comprising at least one heteroatom selected from O, S and N, wherein the aryl can be substituted with at least one substituent selected from the group consisting of halo, alkyl, alkoxy, and phenoxy groups; or R$^3$ represents a benzoyl group; or furanoyl group.

2. The compound selected from the group consisting of pyrazolylmethylamine-piperazine derivatives and their pharmaceutically acceptable salts thereof according to claim 1, wherein Y represents —(CH$_2$)$_n$—C(O)—; or —C(O)—(CH$_2$)$_n$—, wherein n is an integer of 1-4;

R$^1$ and R$^2$, which may be same or different, respectively represent a hydrogen atom; C$_1$-C$_8$ alkyl; phenyl; benzyl; phenethyl; or heteroaryl groups selected from furyl, pyridyl, pyrimidyl, and piperonyl groups;

R$^3$ represents phenyl; benzyl; benzhydryl; benzoyl; heteroaryl selected from furyl, pyridyl, pyrimidyl, and piperonyl groups; or furanoyl groups;

wherein the phenyl or benzyl groups in R$^1$, R$^2$, and R$^3$ can be respectively substituted with 1-3 substituents selected from the group consisting of halo, hydroxy, nitro, cyano, carboxyl, C$_1$-C$_8$ alkyl, C$_1$-C$_8$ haloalkyl, C$_1$-C$_8$ thioalkyl, C$_1$-C$_8$ alkoxy groups, and 5-7 membered heterocycloalkyl groups comprising at least one heteroatom selected from O, S and N;

wherein the heterocycloalkyl groups represent 5-10 membered monocyclic or fused rings comprising at least one heteroatom selected from O, S, and N.

3. A compound selected from the group consisting of pyrazolylmethylamine-piperazine derivatives represented by the following formula 1 and their pharmaceutically acceptable salts thereof,

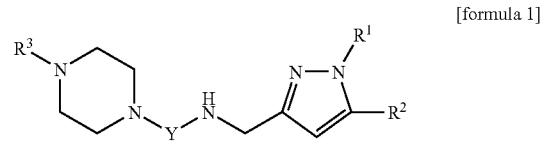

[formula 1]

wherein Y represents —CH$_2$—C(O)—; or —C(O)—CH$_2$—;

R$^1$ represents a hydrogen atom, phenyl, carboxylphenyl, C$_1$-C$_8$ alkoxyphenyl, or benzyl groups;

R$^2$ represents C$_1$-C$_8$ alkyl group; phenyl group; phenyl group substituted with 1-3 substituents selected from the group consisting of C$_1$-C$_8$ alkyl, C$_1$-C$_8$ thioalkyl, C$_1$-C$_8$ alkoxy, piperidinyl and morpholinyl groups; phenethyl; furyl group; or pyridyl group; and R³ represents phenyl; phenyl substituted with 1-3 substituents selected from the group consisting of hydroxy, cyano and C₁-C₈ alkyl groups; benzyl group; benzyl group substituted with 1-3 substituents selected from the group consisting of phenyl, benzyl, halo, C₁-C₈ alkyl, C₁-C₈ haloalkyl, and C₁-C₈ alkoxy groups; heteroaryl group selected from the group consisting of furyl, pyridyl, pyrimidyl, and piperonyl groups; benzhydryl group; benzhydryl group substituted with halogen; or furanoyl group.

4. A compound selected from the group consisting of pyrazolylmethylamine-piperazine derivatives represented by the following formula 1 and their pharmaceutically acceptable salts thereof,

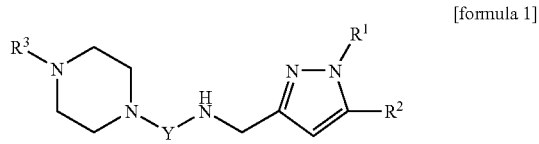

[formula 1]

wherein Y represents —CH₂—C(O)—, or —C(O)—CH₂—;

R¹ represents a hydrogen atom, phenyl, carboxyphenyl, methoxyphenyl, or benzyl group;

R² represents methyl, ethyl, n-propyl, isopropyl, isobutyl, tert-butyl, phenyl, toluoyl, methoxyphenyl, thiomethylphenyl, morpholinophenyl, piperidinophenyl, phenethyl, furyl, or pyridyl group; and R³ represents phenyl, hydroxyphenyl, cyanophenyl, dimethylphenyl, benzyl, halobenzyl, dihalobenzyl, methylbenzyl, dimethylbenzyl, trimethylbenzyl, trifluoromethylbenzyl, trimethoxybenzyl, benzhydryl, (halolphenyl)(phenyl)methyl, pyridyl, pyrimidyl, piperonyl, or furanoyl group.

5. A compound selected from the group consisting of pyrazolylmethylamine-piperazine derivatives represented by the following formula 1 and their pharmaceutically acceptable salts thereof,

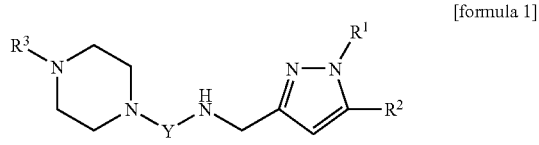

[formula 1]

wherein said compound includes:
3-{[4-(2,3-dimethyl)phenylpiperazin-1-yl]methylcarboxamido}methyl-5-methyl-1-phenyl-1H-pyrazole (Compound No. 1);
3-[(4-phenylpiperazin-1-yl)methylcarboxamido]methyl-5-methyl-1-phenyl-1H-pyrazole (Compound No. 2);
3-[(4-benzhydrylpiperazin-1-yl)methylcarboxamido]methyl-5-methyl-1-phenyl-1H-pyrazole (Compound No. 3);
3-{[4-(2,4-dimethylphenyl)piperazin-1-yl]methylcarboxamido}methyl-5-methyl-1-phenyl-1H-pyrazole (Compound No. 4);
3-{[4-(3-trifluoromethyl)benzylpiperazin-1-yl]methylcarboxamido}methyl-5-methyl-1-phenyl-1H-pyrazole (Compound No. 5);
3-{[4-(3,4-dichlorobenzyl)piperazin-1-yl]methylcarboxamido}methyl-5-methyl-1-phenyl-1H-pyrazole (Compound No. 6);
3-{[4-(4-trifluoromethyl)benzylpiperazin-1-yl]methylcarboxamido}methyl-5-methyl-1-phenyl-1H-pyrazole (Compound No. 7);
3-{[4-(2,3,4-trimethoxy)benzylpiperazin-1-yl]methylcarboxamido}methyl-5-methyl-1-phenyl-1H-pyrazole (Compound No. 8);
3-[(4-phenylpiperazin-1-yl)methylcarboxamido]methyl-5-isobutyl-1-phenyl-1H-pyrazole (Compound No. 9);
3-{[4-(2,3-dimethylphenyl)piperazin-1-yl]methylcarboxamido}methyl-5-isobutyl-1-phenyl-1H-pyrazole (Compound No. 10);
3-[(4-phenylpiperazin-1-yl)methylcarboxamido]methyl-5-furyl-1-phenyl-1H-pyrazole (Compound No. 11);
3-{[4-(2,3-dimethylphenyl)piperazin-1-yl]methylcarboxamido}methyl-5-furyl-1-phenyl-1H-pyrazole (Compound No. 12);
3-{[4-(3-trifluoromethylbenzyl)piperazin-1-yl]methylcarboxamido}methyl-5-furyl-1-phenyl-1H-pyrazole (Compound No. 13);
3-{[4-(4-trifluoromethylbenzyl)piperazin-1-yl]methylcarboxamido}methyl-5-furyl-1-phenyl-1H-pyrazole (Compound No. 14);
3-{[4-(3-trifluoromethylbenzyl)piperazin-1-yl]methylcarboxamido}methyl-5-isobutyl-1-phenyl-1H-pyrazole (Compound No. 15);
3-{[4-(4-trifluoromethylbenzyl)piperazin-1-yl]methylcarboxamido}methyl-5-isobutyl-1-phenyl-1H-pyrazole (Compound No. 16);
3-{[4-(2,3,4-trimethoxy)benzylpiperazin-1-yl]methylcarboxamido}methyl-5-isobutyl-1-phenyl-1H-pyrazole (Compound No. 17);
3-{[4-(2,3,4-trimethoxy)benzylpiperazin-1-yl]methylcarboxamido}methyl-5-furyl-1-phenyl-1H-pyrazole (Compound No. 18);
3-[(4-benzhydrylpiperazin-1-yl)methylcarboxamido]methyl-5-isobutyl-1-phenyl-1H-pyrazole (Compound No. 19);
3-[(4-benzhydrylpiperazin-1-yl)methylcarboxamido]methyl-5-furyl-1-phenyl-1H-pyrazole (Compound No. 20);
3-[(4-piperonylpiperazin-1-yl)methylcarboxamido]methyl-5-isobutyl-1-phenyl-1H-pyrazole (Compound No. 21);
3-[(4-piperonylpiperazin-1-yl)methylcarboxamido]methyl-5-furyl-1-phenyl-1H-pyrazole (Compound No. 22);
3-{[4-(3,4-dichloro)benzylpiperazin-1-yl]methylcarboxamido}methyl-5-furyl-1-phenyl-1H-pyrazole (Compound No. 23);
3-{[4-(3,4-dichloro)benzylpiperazin-1-yl]methylcarboxamido}methyl-5-isobutyl-1-phenyl-1H-pyrazole (Compound No. 24);
3-{[4-(4-chlorophenyl)(phenyl)methylpiperazin-1-yl]methylcarboxamido}methyl-5-methyl-1-phenyl-1H-pyrazole (Compound No. 25);
3-{[4-(4-chlorophenyl)(phenyl)methylpiperazin-1-yl]methylcarboxamido}methyl-5-furyl-1-phenyl-1H-pyrazole (Compound No. 26);
3-[(4-phenylpiperazin-1-yl)methylcarboxamido]methyl-5-propyl-1-phenyl-1H-pyrazole (Compound No. 27);
3-{[4-(2,3-dimethyl)phenylpiperazin-1-yl]methylcarboxamido}methyl-5-propyl-1-phenyl-1H-pyrazole (Compound No. 28);

3-{[4-(2,4-dimethyl)phenylpiperazin-1-yl]methylcarboxamido}methyl-5-propyl-1-phenyl-1H-pyrazole (Compound No. 29);

3-[(4-benzhydrylpiperazin-1-yl)methylcarboxamido]methyl-5-propyl-1-phenyl-1H-pyrazole (Compound No. 30);

3-{[4-(3-trifluoromethyl)benzylpiperazin-1-yl]methylcarboxamido}methyl-5-propyl-1-phenyl-1H-pyrazole (Compound No. 31);

3-{[4-(4-trifluoromethyl)benzylpiperazin-1-yl]methylcarboxamido}methyl-5-propyl-1-phenyl-1H-pyrazole (Compound No. 32);

3-[(4-piperonylpiperazin-1-yl)methylcarboxamido]methyl-5-propyl-1-phenyl-1H-pyrazole (Compound No. 33);

3-{[4-(2-pyridyl)piperazin-1-yl]methylcarboxamido}methyl-5-methyl-1-phenyl-1H-pyrazole (Compound No. 34);

3-{[4-(2-pyrimidyl)piperazin-1-yl]methylcarboxamido}methyl-5-methyl-1-phenyl-1H-pyrazole (Compound No. 35);

3-{[4-(2-pyridyl)piperazin-1-yl]methylcarboxamido}methyl-5-isobutyl-1-phenyl-1H-pyrazole (Compound No. 36);

3-{[4-(2-pyrimidyl)piperazin-1-yl]methylcarboxamido}methyl-5-isobutyl-1-phenyl-1H-pyrazole (Compound No. 37);

3-{[4-(2-(pyridyl)piperazin-1-yl]methylcarboxamido}methyl-5-furyl-1-phenyl-1H-pyrazole (Compound No. 38);

3-{[4-(2-pyrimidyl)piperazin-1-yl]methylcarboxamido}methyl-5-furyl-1-phenyl-1H-pyrazole (Compound No. 39);

3-{[4-(4-t-butyl)benzylpiperazin-1-yl]methylcarboxamido}methyl-5-methyl-1-phenyl-1H-pyrazole (Compound No. 40);

3-{[4-(2,4,6-trimethyl)benzylpiperazin-1-yl]methylcarboxamido}methyl-5-methyl-1-phenyl-1H-pyrazole (Compound No. 41);

3-{[4-(4-t-butyl)benzylpiperazin-1-yl]methylcarboxamido}methyl-5-isobutyl-1-phenyl-1H-pyrazole (Compound No. 42);

3-{[4-(2,4,6-trimethyl)benzylpiperazin-1-yl]methylcarboxamido}methyl-5-isobutyl-1-phenyl-1H-pyrazole (Compound No. 43);

3-{[4-(2,3-dimethylphenyl)piperazin-1-yl]methylcarboxamido}methyl-5-(4-methoxy)phenyl-1-phenyl-1H-pyrazole (Compound No. 44);

3-{[4-(2,4-dimethylphenyl)piperazin-1-yl]methylcarboxamido}methyl-5-(4-methoxy)phenyl-1-phenyl-1H-pyrazole (Compound No. 45);

3-[4-furoylpiperazin-1-yl)methylcarboxamido]methyl-5-methyl-1-phenyl-1H-pyrazole (Compound No. 46);

3-[(4-furoylpiperazin-1-yl)methylcarboxamido]methyl-5-isobutyl-1-phenyl-1H-pyrazole (Compound No. 47);

3-{[4-(2-cyanophenyl)piperazin-1-yl]methylcarboxamido}methyl-5-methyl-1-phenyl-1H-pyrazole (Compound No. 48);

3-{[4-(2-cyanophenyl)piperazin-1-yl]methylcarboxamido}methyl-5-propyl-1-phenyl-1H-pyrazole (Compound No. 49);

3-{[4-(2,3-dimethylphenyl)piperazin-1-yl]methylcarboxamido}methyl-5-(4-thiomethyl)phenyl-1-phenyl-1H-pyrazole (Compound No. 50);

3-{[4-(2,4-dimethylphenyl)piperazin-1-yl]methylcarboxamido}methyl-5-(4-thiomethyl)phenyl-1-phenyl-1H-pyrazole (Compound No. 51);

3-{[4-(3-hydroxyphenyl)piperazin-1-yl]methylcarboxamido}methyl-5-methyl-1-phenyl-1H-pyrazole (Compound No. 52);

3-{[4-(3-hydroxyphenyl)piperazin-1-yl]methylcarboxamido}methyl-5-isobutyl-1-phenyl-1H-pyrazole (Compound No. 53);

3-[(4-phenylpiperazin-1-yl)methylcarboxamido]methyl-5-(4-thiomethyl)phenyl-1-phenyl-1H-pyrazole (Compound No. 54);

3-{[4-(3-hydroxyphenyl)piperazin-1-yl]methylcarboxamido}methyl-5-(4-thiomethyl)phenyl-1-phenyl-1H-pyrazole (Compound No. 55);

3-{[4-(2,3-dimethylphenyl)piperazin-1-yl]methylcarboxamido}methyl-5-propyl-1-(4-carboxyl)phenyl-1H-pyrazole (Compound No. 56);

3-{[4-(2,3-dimethylphenyl)piperazin-1-yl]methylcarboxamido}methyl-5-isobutyl-1-(4-carboxyl)phenyl-1H-pyrazole (Compound No. 57);

3-{[4-(2,3-dimethylphenyl)piperazin-1-yl]methylcarboxamido}methyl-5-methyl-1-(4-carboxyl)phenyl-1H-pyrazole (Compound No. 58);

3-{[4-(2,3-dimethylphenyl)piperazin-1-yl]methylcarboxamido}methyl-5-(4-morpholino)phenyl-1-phenyl-1H-pyrazole (Compound No. 59);

3-[(4-phenylpiperazin-1-yl)methylcarboxamido]methyl-5-(4-morpholino)phenyl-1-phenyl-1H-pyrazole (Compound No. 60);

3-{[4-(2,4-dimethylphenyl)piperazin-1-yl]methylcarboxamido}methyl-5-(4-morpholino)phenyl-1-phenyl-1H-pyrazole (Compound No. 61);

3-{[4-(3-trifluorobenzyl)piperazin-1-yl]methylcarboxamido}methyl-5-(4-morpholino)phenyl-1-phenyl-1H-pyrazole (Compound No. 62);

3-{[4-(4-trifluorobenzyl)piperazin-1-yl]methylcarboxamido}methyl-5-(4-morpholino)phenyl-1-phenyl-1H-pyrazole (Compound No. 63);

3-{[4-(2,3-dimethylphenyl)piperazin-1-yl]carbonylmethylamino}methyl-5-methyl-1-phenyl-1H-pyrazole (Compound No. 64);

3-[(4-benzhydrylpiperazin-1-yl)carbonylmethylamino]methyl-5-methyl-1-phenyl-1H-pyrazole (Compound No. 65);

3-[(4-phenylpiperazin-1-yl)carbonylmethylamino]methyl-5-methyl-1-phenyl-1H-pyrazole (Compound No. 66);

3-[(4-phenylpiperazin-1-yl)carbonylmethylamino]methyl-5-isobutyl-1-phenyl-1H-pyrazole (Compound No. 67);

3-[(4-benzhydrylpiperazin-1-yl)carbonylmethylamino]methyl-5-isobutyl-1-phenyl-1H-pyrazole (Compound No. 68);

3-{[4-(2,4-dimethylphenyl)piperazin-1-yl]carbonylmethylamino}methyl-5-isobutyl-1-phenyl-1H-pyrazole (Compound No. 69);

3-[(4-phenylpiperazin-1-yl)carbonylmethylamino]methyl-5-furyl-1-phenyl-1H-pyrazole (Compound No. 70);

3-[(4-benzhydrylpiperazin-1-yl)carbonylmethylamino]methyl-5-furyl-1-phenyl-1H-pyrazole (Compound No. 71);

3-{[4-(2,4-dimethyl)phenylpiperazin-1-yl]carbonylmethylamino}methyl-5-furyl-1-phenyl-1H-pyrazole (Compound No. 72);

3-{[4-(2,4-dimethyl)phenylpiperazin-1-yl]carbonylmethylamino}methyl-5-methyl-1-phenyl-1H-pyrazole (Compound No. 73);

3-{[4-(3,4-dichloro)benzylpiperazin-1-yl]
  carbonylmethylamino}methyl-5-methyl-1-phenyl-1H-
  pyrazole (Compound No. 74);
3-{[4-(3,4-dichlorobenzyl)piperazin-1-yl]
  carbonylmethylamino}methyl-5-isobutyl-1-phenyl-
  1H-pyrazole (Compound No. 75);
3-{[4-(2,3-dimethylphenyl)piperazin-1-yl]
  carbonylmethylamino}methyl-5-isobutyl-1-phenyl-
  1H-pyrazole (Compound No. 76);
3-{[4-(2,3-dimethylphenyl)piperazin-1-yl]
  carbonylmethylamino}methyl-5-furyl-1-phenyl-1H-
  pyrazole (Compound No. 77);
3-{[4-(3,4-dichlorobenzyl)piperazin-1-yl]
  carbonylmethylamino}methyl-5-furyl-1-phenyl-1H-
  pyrazole (Compound No. 78);
3-[(4-piperonylpiperazin-1-yl)carbonylmethylamino]me-
  thyl-5-isobutyl-1-phenyl-1H-pyrazole (Compound No.
  79);
3-[(4-piperonylpiperazin-1-yl)carbonylmethylamino]me-
  thyl-5-furyl-1-phenyl-1H-pyrazole (Compound No.
  80);
3-{[4-(2,3,4-trimethoxybenzyl)piperazin-1-yl]
  carbonylmethylamino}methyl-5-isobutyl-1-phenyl-
  1H-pyrazole (Compound No. 81);
3-{[4-(2,3-dimethylphenyl)piperazin-1-yl]
  carbonylmethylamino}methyl-5-propyl-1-phenyl-1H-
  pyrazole (Compound No. 82);
3-{[4-(2,4-dimethylphenyl)piperazin-1-yl]
  carbonylmethylamino}methyl-5-propyl-1-phenyl-1H-
  pyrazole (Compound No. 83);
3-[(4-phenylpiperazin-1-yl)carbonylmethylamino]me-
  thyl-5-propyl-1-phenyl-1H-pyrazole (Compound No.
  84);
3-[(4-phenylpiperazin-1-yl)methylcarboxamido]methyl-
  5-methyl-1-[(4-methoxy)phenyl]-1H-pyrazole (Compound No. 85);
3-[(4-phenylpiperazin-1-yl)methylcarboxamido]methyl-
  5-[(4-piperidino)phenyl]-1-phenyl-1H-pyrazole (Compound No. 86);
3-[(4-phenylpiperazin-1-yl)methylcarboxamido]methyl-
  5-isobutyl-1-[(4-methoxy)phenyl]-1H-pyrazole (Compound No. 87);
3-{(4-(2,3-dimethylphenyl)piperazin-1-yl]
  methylcarboxamido}methyl-5-isobutyl-1-[(4-methoxy)phenyl]-1H-pyrazole (Compound No. 88);
3-[(4-phenylpiperazin-1-yl)methylcarboxamido]methyl-
  5-(2-pyridyl)-1-phenyl-1H-pyrazole (Compound No.
  89);
3-{(4-(2,3-dimethylphenyl)piperazin-1-yl]
  methylcarboxamido}methyl-5-(2-pyridyl)-1-phenyl-
  1H-pyrazole (Compound No. 90);
3-[(4-phenylpiperazin-1-yl)methylcarboxamido]methyl-
  5-[(4-methyl)phenyl]-1-phenyl-1H-pyrazole (Compound No. 91);
3-{(4-(2,3-dimethylphenyl)piperazin-1-yl]
  methylcarboxamido}methyl-5-[(4-methyl)phenyl]-1-
  phenyl-1H-pyrazole (Compound No. 92);
3-[(4-phenylpiperazin-1-yl)methylcarboxamido]methyl-
  5-methyl-1-benzyl-1H-pyrazole (Compound No. 93);
3-{(4-(2,3-dimethylphenyl)piperazin-1-yl]
  methylcarboxamido}methyl-5-methyl-1-benzyl-1H-
  pyrazole (Compound No. 94);
3-{[4-(2,3-dimethylphenyl)piperazin-1-yl]
  carbonylmethylamino}methyl-5-methyl-1H-pyrazole
  (Compound No. 95);
and their pharmaceutically acceptable salts thereof.

6. A pharmaceutical composition for the prevention and treatment of diseases selected from the group consisting of cerebral disease, cardiac diseases, and pain-related diseases by antagonistic activity of T-type calcium channel comprising a pyrazolylmethylamine-piperazine derivative or its pharmaceutically acceptable salt thereof according to claim 1 as an active ingredient;

wherein the cerebral disease comprises epilepsy, depression, Parkinson's disease, dementia, or sleep disorder;

wherein the cardiac diseases comprise hypertension, cardiac arrhythmia, angina pectoris, myocardial infarction or congestive heart failure; and wherein the pain-related diseases comprise chronic pains, acute pains, or neuropathic pains.

7. A method for manufacturing pyrazolylmethylamine-piperazine derivatives represented by the formula 1a below by performing a coupling reaction between a haloacetylpiperazine compound represented by the formula 2 below and a pyrazolylmethylamine compound represented by the formula 3 below:

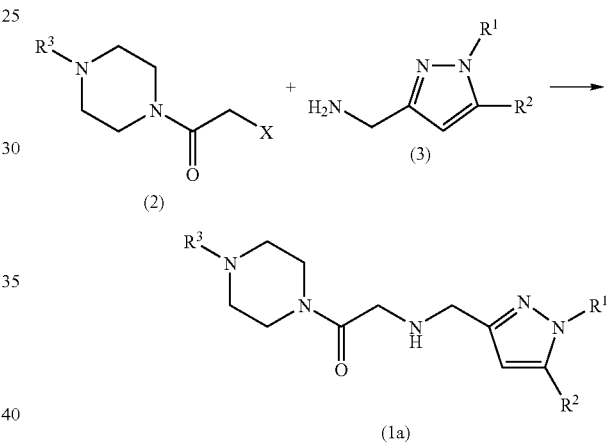

wherein said $R^1$, $R^2$, and $R^3$ are the same as defined in claim 1, and X represents a halogen atom.

8. A method for manufacturing pyrazolylmethylamine-piperazine derivatives represented by the formula 1b below by performing a coupling reaction between a piperazine compound represented by the formula 4 below and a pyrazolylmethylcarbamoylmethyl halide compound represented by the formula 5 below:

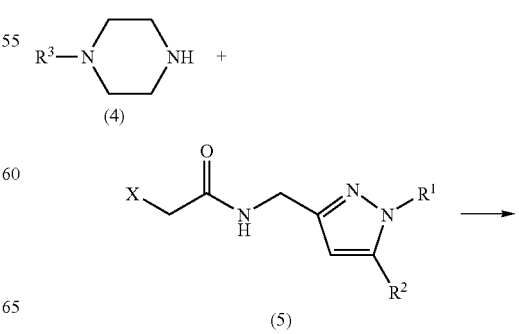

-continued

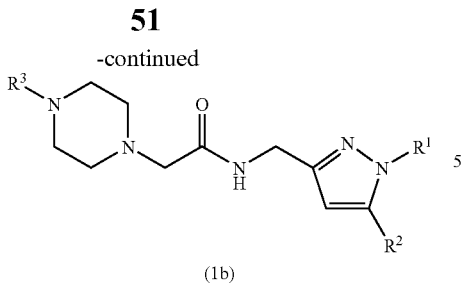

(1b)

wherein said $R^1$, $R^2$, and $R^3$ are the same as defined in claim 1, and X represents a halogen atom.

9. The method for manufacturing pyrazolylmethylamine-piperazine derivatives according to claim 8, wherein said pyrazolylmethylcarbamoylmethyl halide compound represented by the above formula 5 is manufactured by a process comprising:
  (a) converting a pyrazolaldehyde compound represented by the formula 7 below to a pyrazoloxime compound represented by the formula 8 below;
  (b) converting said pyrazoloxime compound represented by the formula 8 below to a pyrazolylamine compound represented by the formula 9 below; and
  (c) converting said pyrazolylamine compound represented by the formula 9 below to a pyrazolylmethylcarbamoylmethyl halide compound represented by the formula 5 below:

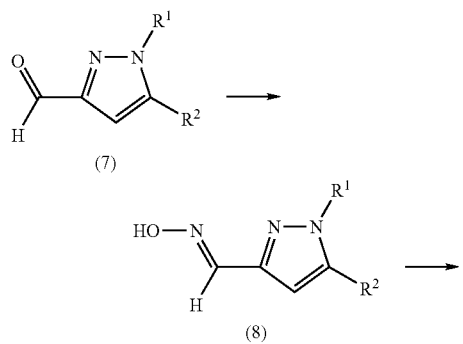

-continued

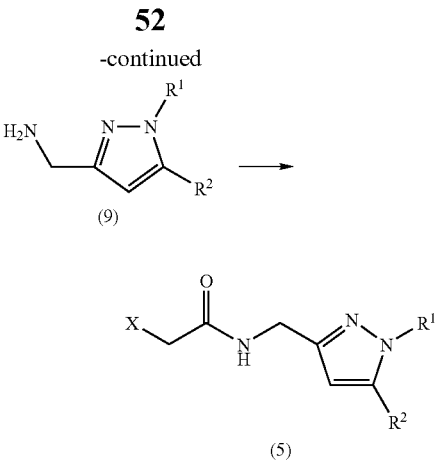

wherein said $R^1$ and $R^2$ are the same as defined in claim 1, and X represents a halogen atom.

10. A compound selected from the group consisting of pyrazolylmethylamine-piperazine derivatives represented by the following formula 1 and their pharmaceutically acceptable salts thereof,

[formula 1]

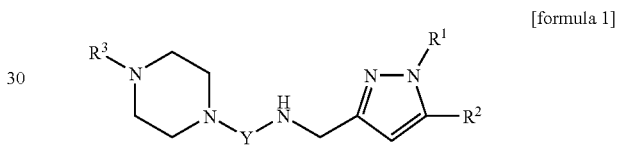

wherein the compound is 3-{[4-(2,3-dimethyl)phenylpiperazin-1-yl]methylcarboxamido}methyl-5-methyl-1-phenyl-1H-pyrazole.

* * * * *